(12) United States Patent
Eisen et al.

(10) Patent No.: US 12,350,167 B2
(45) Date of Patent: Jul. 8, 2025

(54) INTERVERTEBRAL CAGES WITH DEPLOYABLE ANCHORS

(71) Applicant: EIT Emerging Implant Technologies GmbH, Wurmlingen (DE)

(72) Inventors: Guntmar Eisen, Wurmlingen (DE); Detlev Ganter, Wurmlingen (DE); Stephan Geiger, Wurmlingen (DE); Matthew F. Gornet, Chesterfield, MO (US)

(73) Assignee: EIT Emerging Implant Technologies GmbH, Wurmlingen (DE)

( * ) Notice: Subject to any disclaimer, the term of this patent is extended or adjusted under 35 U.S.C. 154(b) by 275 days.

(21) Appl. No.: 17/412,573

(22) Filed: Aug. 26, 2021

(65) Prior Publication Data

US 2021/0378839 A1    Dec. 9, 2021

Related U.S. Application Data

(63) Continuation of application No. 16/292,568, filed on Mar. 5, 2019, now Pat. No. 11,135,069.

(60) Provisional application No. 62/639,237, filed on Mar. 6, 2018.

(51) Int. Cl.
  *A61F 2/44* (2006.01)
  *A61F 2/46* (2006.01)
  *A61F 2/30* (2006.01)

(52) U.S. Cl.
  CPC ............ *A61F 2/4455* (2013.01); *A61F 2/447* (2013.01); *A61F 2/4611* (2013.01); *A61F 2002/30579* (2013.01); *A61F 2002/30604* (2013.01); *A61F 2/30771* (2013.01); *A61F 2/442* (2013.01)

(58) Field of Classification Search
  CPC .............................. A61F 2/4455–2/447; A61F 2220/0008–2220/0016; A61F 2002/30579
  USPC .................................. 623/17.11, 17.15, 17.16
  See application file for complete search history.

(56) References Cited

U.S. PATENT DOCUMENTS

| | | | |
|---|---|---|---|
| 6,102,950 A * | 8/2000 | Vaccaro | A61F 2/4637 606/247 |
| 6,113,638 A | 9/2000 | Williams et al. | |
| 6,179,873 B1 * | 1/2001 | Zientek | A61F 2/4657 623/17.11 |
| 6,527,803 B1 | 3/2003 | Crozet et al. | |
| 6,800,092 B1 | 10/2004 | Williams et al. | |
| 9,241,809 B2 | 1/2016 | McDonough et al. | |
| 2005/0049590 A1 | 3/2005 | Alleyne et al. | |
| 2009/0265007 A1 | 10/2009 | Colleran | |
| 2012/0029637 A1 | 2/2012 | Ragab et al. | |
| 2014/0121773 A1 | 5/2014 | Patel et al. | |

(Continued)

FOREIGN PATENT DOCUMENTS

CN    102438536 A    5/2012

*Primary Examiner* — Eduardo C Robert
*Assistant Examiner* — David C Comstock
(74) *Attorney, Agent, or Firm* — BakerHostetler

(57) ABSTRACT

Disclosed are interbody fusion spacers, or cages, for insertion between adjacent vertebrae. The cages may have integrated and deployable anchors that allow the cage to have a first, insertion configuration characterized by a reduced size to facilitate insertion through a narrow access passage and into the intervertebral space. Once implanted, the anchors of the cages may be deployed to enable better fixation to bone. The cages may promote fusion to further enhance spine stability by immobilizing the adjacent vertebral bodies.

20 Claims, 11 Drawing Sheets

(56) References Cited

U.S. PATENT DOCUMENTS

| | | |
|---|---|---|
| 2014/0330387 A1* | 11/2014 | Arnin .................... A61F 2/4455 |
| | | 623/17.16 |
| 2015/0202051 A1 | 7/2015 | Tanaka et al. |
| 2015/0238324 A1* | 8/2015 | Nebosky ............... A61F 2/3094 |
| | | 623/17.16 |
| 2016/0206352 A1 | 7/2016 | Hess et al. |
| 2016/0361176 A1 | 12/2016 | Weiman et al. |
| 2016/0374831 A1 | 12/2016 | Duffield et al. |
| 2017/0056179 A1* | 3/2017 | Lorio ................. B23K 15/0093 |
| 2017/0128226 A1 | 5/2017 | Faulhaber |
| 2017/0165082 A1 | 6/2017 | Faulhaber |
| 2017/0312095 A9 | 11/2017 | Patel et al. |
| 2018/0104068 A1 | 4/2018 | Sack |
| 2018/0116815 A1 | 5/2018 | Kuyler et al. |

* cited by examiner

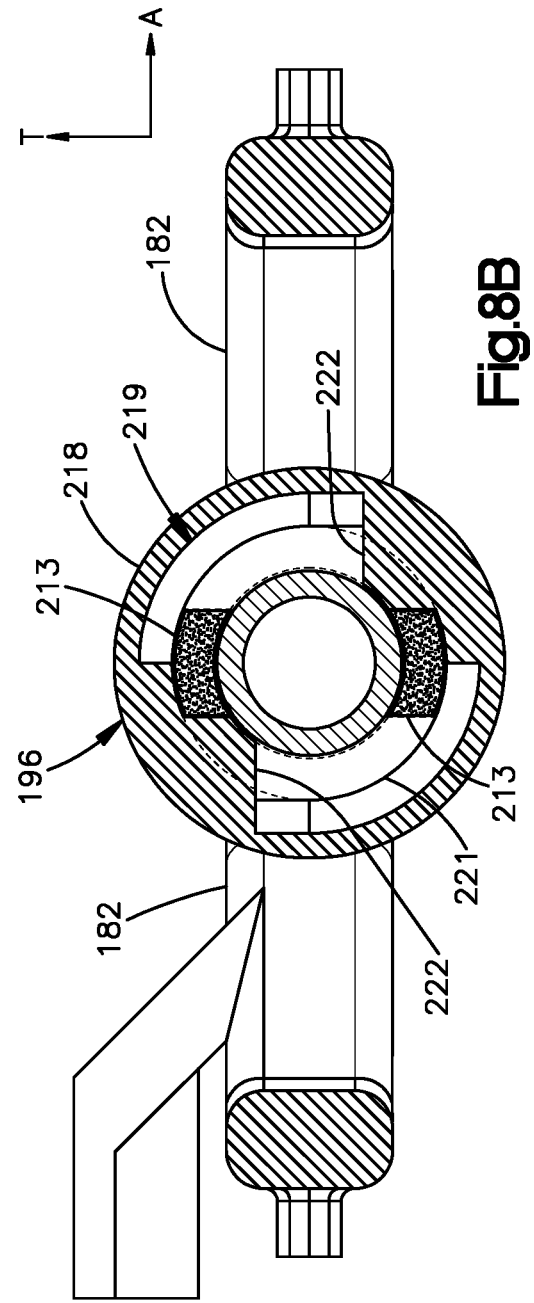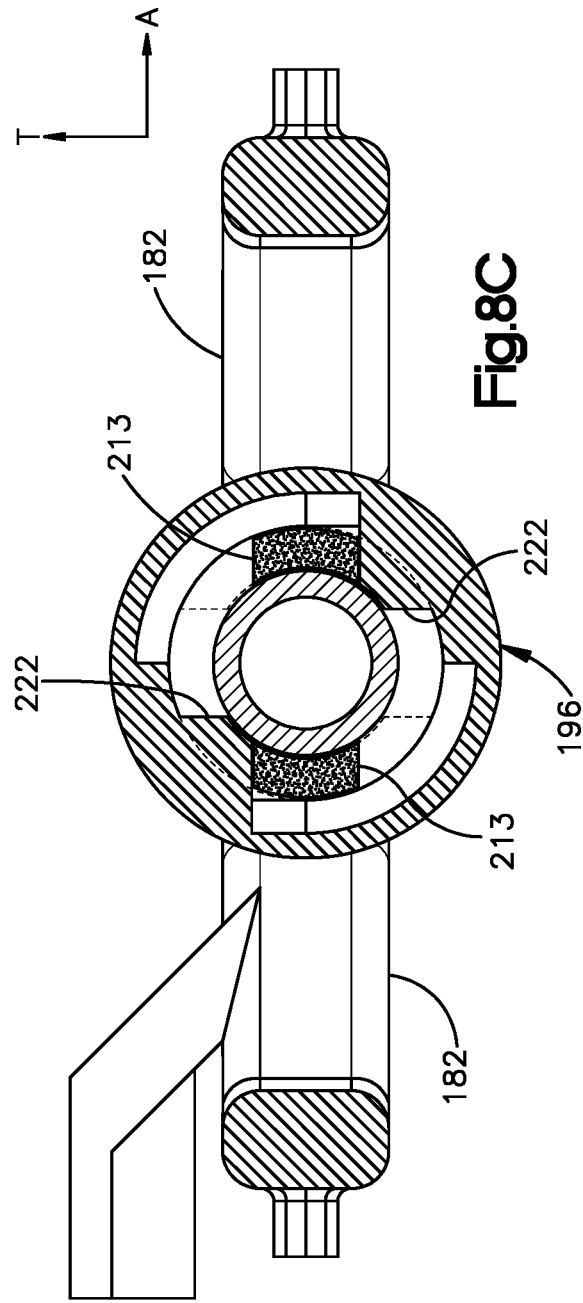

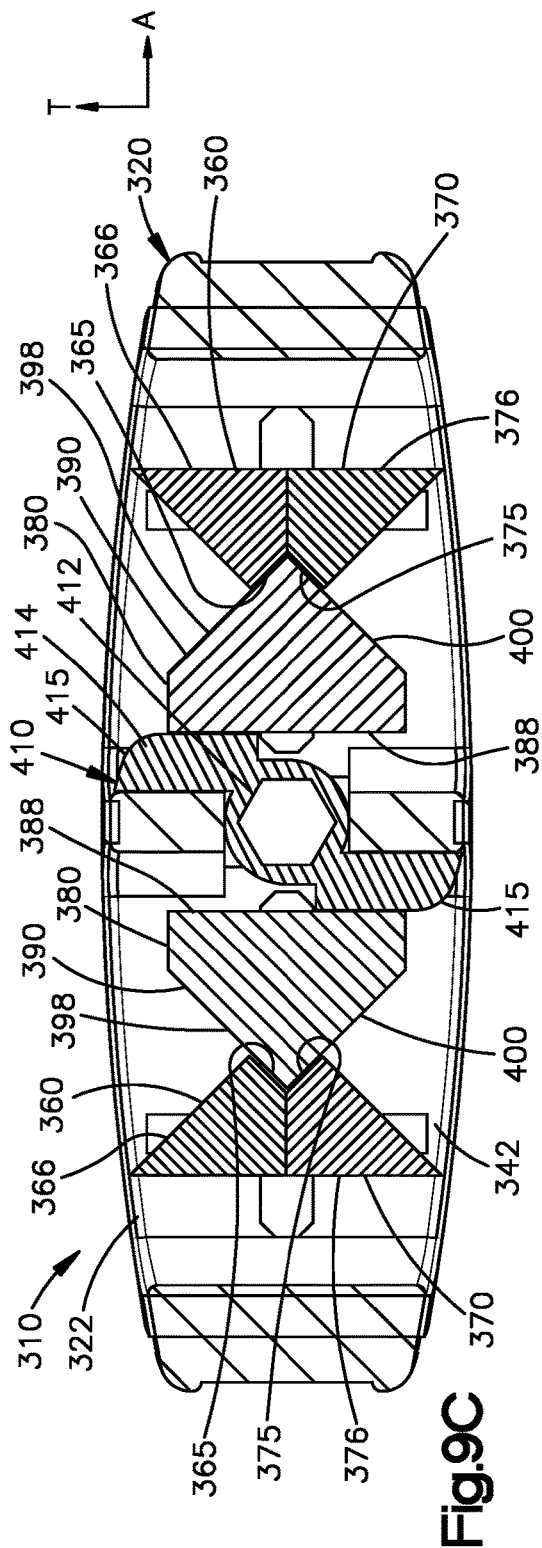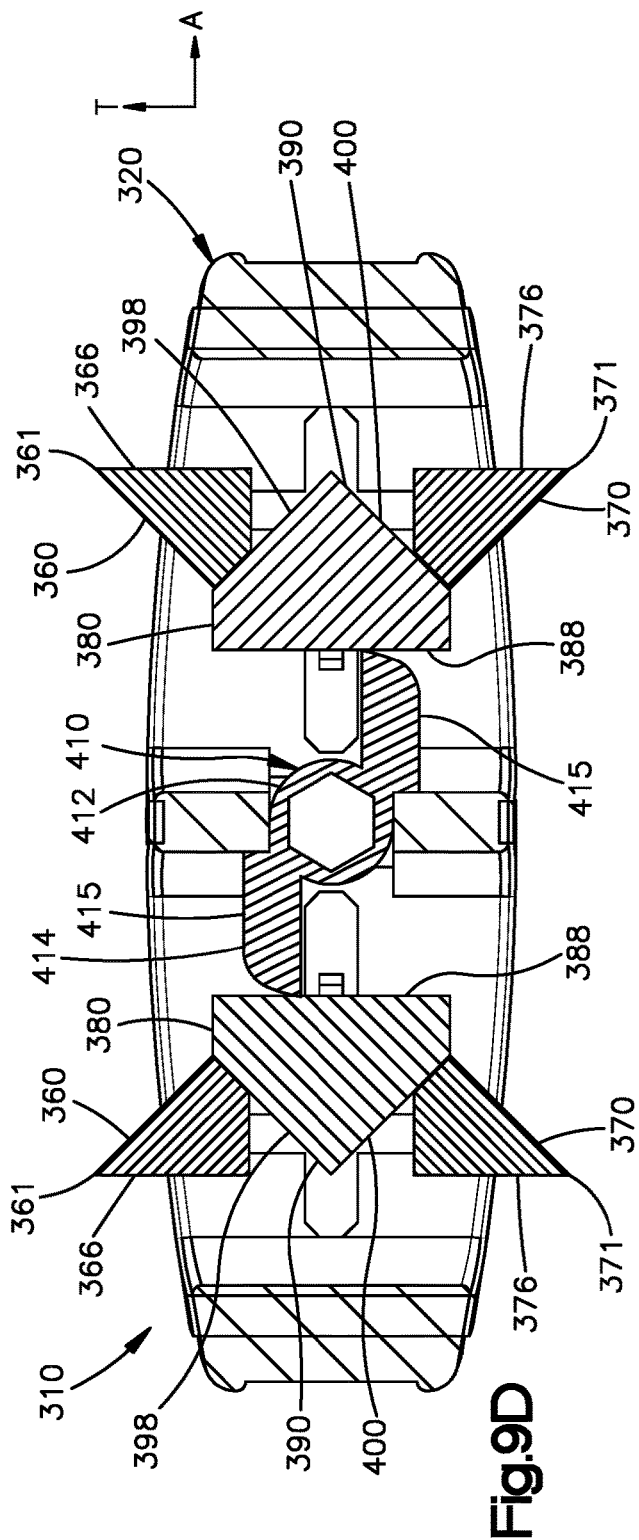

INTERVERTEBRAL CAGES WITH DEPLOYABLE ANCHORS

CROSS-REFERENCE TO RELATED APPLICATIONS

This is a continuation of U.S. patent application Ser. No. 16/292,568 filed Mar. 5, 2019, which claims the benefit of U.S. Patent Application Ser. No. 62/639,237 filed Mar. 6, 2018, the disclosure of which is hereby incorporated by reference as if set forth in its entirety herein.

TECHNICAL FIELD

The present disclosure relates to implantable orthopedic devices, and more particularly to implantable devices for stabilizing the spine. Even more particularly, the present disclosure relates to intervertebral cages having deployable anchors.

BACKGROUND

The use of fusion-promoting interbody implantable devices, often referred to as cages or spacers, is well known as the standard of care for the treatment of certain spinal disorders or diseases. For example, in one type of spinal disorder, the intervertebral disc has deteriorated or become damaged due to acute injury or trauma, disc disease or simply the natural aging process. A healthy intervertebral disc serves to stabilize the spine and distribute forces between vertebrae, as well as cushion the vertebral bodies. A weakened or damaged disc therefore results in an imbalance of forces and instability of the spine, resulting in discomfort and pain. The standard treatment today may involve surgical removal of a portion, or all, of the diseased or damaged intervertebral disc in a process known as a partial or total discectomy, respectively. The discectomy is often followed by the insertion of a cage or spacer to stabilize this weakened or damaged spinal region. This cage or spacer serves to reduce or inhibit mobility in the treated area, in order to avoid further progression of the damage and/or to reduce or alleviate pain caused by the damage or injury. Moreover, these types of cages or spacers serve as mechanical or structural scaffolds to restore and maintain normal disc height, and in some cases, can also promote bony fusion between the adjacent vertebrae.

However, one of the current challenges of these types of procedures is the very limited working space afforded the surgeon to manipulate and insert the cage into the intervertebral area to be treated. Access to the intervertebral space requires navigation around retracted adjacent vessels and tissues such as the aorta, vena cava, dura and nerve roots, leaving a very narrow pathway for access. The opening to the intradiscal space itself is also relatively small. Hence, there are physical limitations on the actual size of the cage that can be inserted without significantly disrupting the surrounding tissue or the vertebral bodies themselves.

Further complicating the issue is the fact that the vertebral bodies are not positioned parallel to one another in a normal spine. There is a natural curvature to the spine due to the angular relationship of the vertebral bodies relative to one another. The ideal cage must be able to accommodate this angular relationship of the vertebral bodies, or else the cage will not sit properly when inside the intervertebral space. An improperly fitted cage would either become dislodged or migrate out of position, and lose effectiveness over time, or worse, further damage the already weakened area.

Thus, it is desirable to provide intervertebral cages or spacers that not only have the mechanical strength or structural integrity to restore disc height or vertebral alignment to the spinal segment to be treated, but also be configured to easily pass through the narrow access pathway into the intervertebral space, while also achieving strong anchorage to bone.

BRIEF SUMMARY

In accordance with on aspect of the present disclosure, spinal implantable devices are disclosed that address one or more of the aforementioned challenges and meet the desired objectives. These spinal implantable devices, or more specifically intervertebral cages or spacers, can be configured with deployable anchors. The cages can include upper and lower plates that are configured to bear against respective endplates of the vertebral bodies. The cages can further include integrated anchors that allow the cage to have a first or insertion configuration characterized by a first reduced size to facilitate insertion through a narrow access passage and into the intervertebral space. The cages may be inserted in the first or insertion configuration into an intervertebral disc space that is defined by the vertebral bodies. The anchors can subsequently be deployed so as to provide greater fixation to the vertebral bodies. These cages can thus be configured to promote fusion to further enhance spine stability by immobilizing the adjacent vertebral bodies with respect to each other.

According to one aspect of the disclosure, the cages can be manufactured using selective laser melting (SLM) techniques, a form of additive manufacturing. The cages can also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral cages of the present disclosure can be formed of multiple, interconnected components that do not require additional external fixation elements to keep the interconnected components together.

Further, cages manufactured in this manner can be devoid of connection seams, whereas devices traditionally manufactured typically include joined seams that connect one component to another. These connection seams can represent weakened areas of the implantable device, particularly when the bonds of these seams wear or break over time with repeated use or under stress. By manufacturing the disclosed implantable devices using additive manufacturing, one of the advantages is that connection seams can be avoided entirely.

Further still, by manufacturing these implantable devices using an additive manufacturing process, all of the internal components of the device remain a complete construct during both the insertion process as well as the expansion process. That is, multiple components are provided together as a collective single unit so that the collective single unit is implanted into the patient, actuated to allow expansion, and then allowed to remain as a collective single unit in situ. In contrast to other cages requiring insertion of external screws or wedges for expansion, in the present embodiments the expansion and blocking components do not need to be inserted into the cage, nor removed from the cage, at any stage during the process. This is because these components are manufactured so as to be captured internally within the cages, and while freely movable within the cage, are already contained within the cage so that no additional insertion or removal is necessary.

In some embodiments, the intervertebral cages can have an engineered cellular porous structure on a portion of, or over the entirety of, the cage. This cellular structure can include a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting, to change the surface of the device on the nano level. One type of etching process may utilize, for example, HF acid treatment.

In accordance with other aspects of the present disclosure, intervertebral cages can also include internal imaging markers that allow the user to properly align the device and generally facilitate insertion through visualization during navigation. The imaging marker shows up as a solid body amongst the mesh under x-ray, fluoroscopy or CT scan, for example.

Another benefit provided by the implantable devices of the present disclosure is that they can be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example Dual-Energy X-ray Absorptiometry (DEXA) data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

In one exemplary embodiment, a spinal implant is provided. The spinal implant may comprise a body including an upper plate configured for placement against an endplate of a first vertebral body, a lower plate configured for placement against an endplate of a second, adjacent vertebral body, and a sidewall connecting the upper and lower plates. Each of the plates can contain embedded bone anchors. For instance, the plates can have slots that contain the embedded bone anchors. The spinal implant can further include an actuator that resides within the body. The actuator can have one or more ramped surfaces configured to deploy the embedded anchors out of the slots when the actuator is engaged. The body can further be configured to engage a driver instrument that is configured to engage the actuator, and actuate the actuator so as to deploy the embedded anchors.

According to one example, the ramped surfaces reside on arms that extend from the actuator. Each of the embedded anchors can include a spring and a protrusion extending therefrom. The protrusion may have a ridge for engaging a notch on an arm of the actuator.

In some examples, the body of the spinal implant can include a porous surface. The porous surface may be on the upper or lower plate, or the porous surface may be on the sidewall. In some embodiments, the protrusion has a sharp bone-piercing edge. In some embodiments, the body can have a tapered end. In some embodiments, the body can comprise four embedded anchors. In some embodiments, there are the same number of anchors extending above the upper plate as there are extending below the lower plate.

Although the following discussion focuses on spinal implants, it will be appreciated that many of the principles may equally be applied to other structural body parts requiring bone repair or bone fusion within a human or animal body, including other joints such as knee, shoulder, ankle or finger joints.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate embodiments of the present disclosure and, together with the description, serve to explain the principles of the disclosure.

FIG. 8B is a sectional end view of the actuator illustrated in FIG. 8A, showing the driver instrument inserted in a first rotational position configured to drive the actuator in an actuation direction to deploy the anchors;

FIG. 8C is a sectional end view of the actuator as illustrated in FIG. 8A, showing the driver instrument rotated to a second rotational position configured to drive the actuator in a reverse direction opposite the actuation direction;

FIG. 9C is a sectional elevation view of the intervertebral cage illustrated in FIG. 9A;

FIG. 9D is a sectional elevation view of the intervertebral cage illustrated in FIG. 9B;

DETAILED DESCRIPTION

Figure 1A:
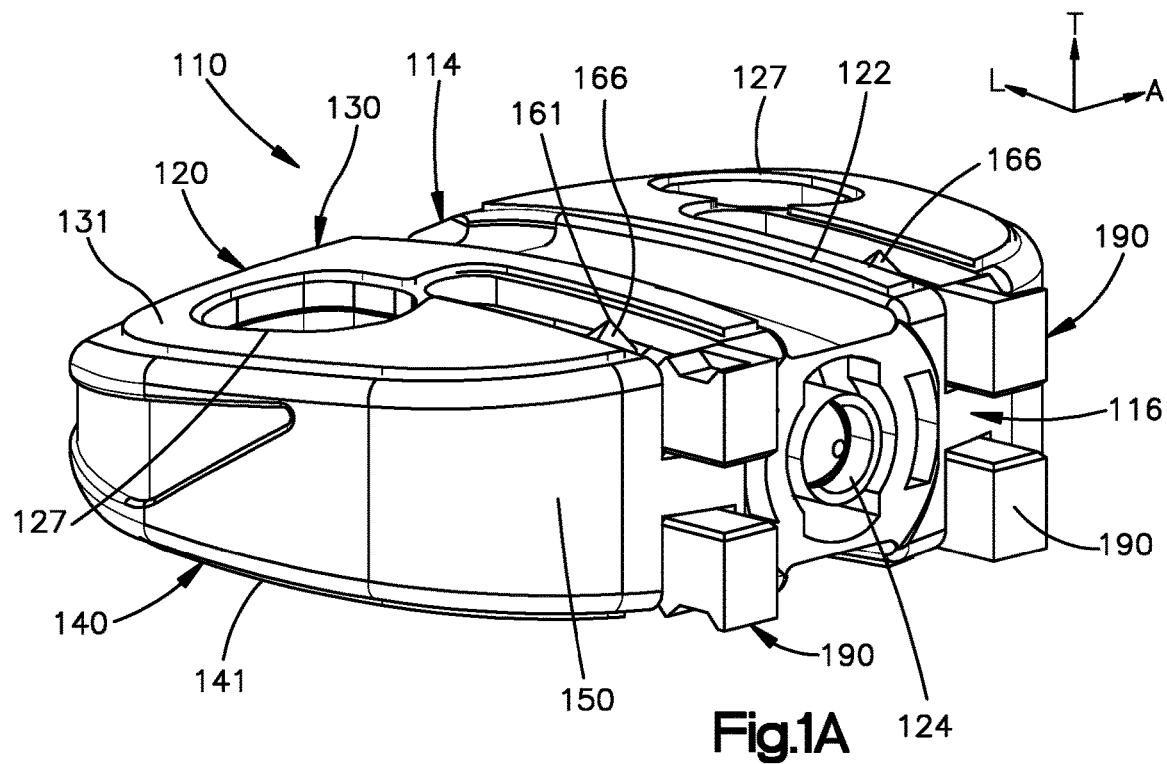
FIG. 1A is a perspective view of an intervertebral cage, shown in a first or insertion configuration.

The present disclosure provides various spinal implant devices, such as interbody fusion spacers, or cages, for insertion between adjacent vertebrae. The devices can be configured for use in either the cervical or lumbar region of the spine. In some embodiments, these devices can be configured as anterior lumbar interbody fusion (ALIF) cages, or lateral lumbar interbody fusion (LLIF) cages, cervical interbody fusion (CIF) device, transforaminal lumbar interbody fusion (TLIF) cages, posterior lumbar interbody fusion (PLIF) cages, and oblique lumbar interbody fusion (OLIF) cages.

The intervertebral cages can be configured to restore and maintain intervertebral height of the spinal segment to be treated, and stabilize the spine by restoring sagittal balance and alignment. In some examples, the intervertebral cages can have integrated and deployable anchors that allow the cage to have a first or insertion configuration characterized by a reduced size to facilitate insertion through a narrow access passage and into the intervertebral disc space. After the cages have been inserted into the intervertebral space in the first or insertion configuration, the integrated anchors can be deployed to further enhance fixation of the intervertebral cage to the vertebral bodies of the vertebrae that define the intervertebral disc space. In some examples, fixing the anchors to the vertebral bodies can immobilize the adjacent vertebral bodies with respect to relative movement, thereby further enhancing spine stability.

The implantable devices can be manufactured using selective laser melting (SLM) techniques, a form of additive manufacturing. The devices may also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral cages of the present disclosure are formed of multiple, interconnected parts that do not require additional external fixation elements to keep together.

Devices manufactured in this manner can be constructed without connection seams, whereas devices traditionally manufactured include joined connection seams that connect the components of the intervertebral cage to each other. These connection seams can often represent weakened areas of the implantable device, particularly when the bonds of these seams wear or break over time with repeated use or under stress. By manufacturing the disclosed implantable devices using additive manufacturing, connection seams can be avoided entirely.

In addition, by manufacturing these devices using an additive manufacturing process, all of the internal components of the device can define a complete construct during both the insertion process as well as the expansion process. That is, multiple components of the intervertebral cage can be provided together as a collective single unit so that the collective single unit is inserted into the patient, actuated to allow expansion, and then allowed to remain as a collective single unit in situ. In contrast to other cages requiring insertion of external screws or wedges for expansion, in certain examples the expansion and blocking components do not need to be inserted into the cage, nor removed from the cage, at any stage during the process. This is because these components are manufactured so as to be captured internally within the cages, and while freely movable within the cage, are already contained within the cage so that no additional insertion or removal is necessary.

In some embodiments, the cages can have an engineered cellular porous structure on a portion of, or over the entirety of, the cage. This cellular structure can include a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting, to change the surface of the device on the nano level. One type of etching process may utilize, for example, HF acid treatment.

In addition, these cages can also include internal imaging markers that allow the user to properly align the cage and generally facilitate insertion through visualization during navigation. The imaging marker shows up as a solid body amongst the mesh under x-ray, fluoroscopy or CT scan, for example.

Another benefit provided by the implantable devices of the present disclosure is that they can be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, Dual-Energy X-ray Absorptiometry (DEXA) data can also allow implantable devices described herein to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

Figure 1B:
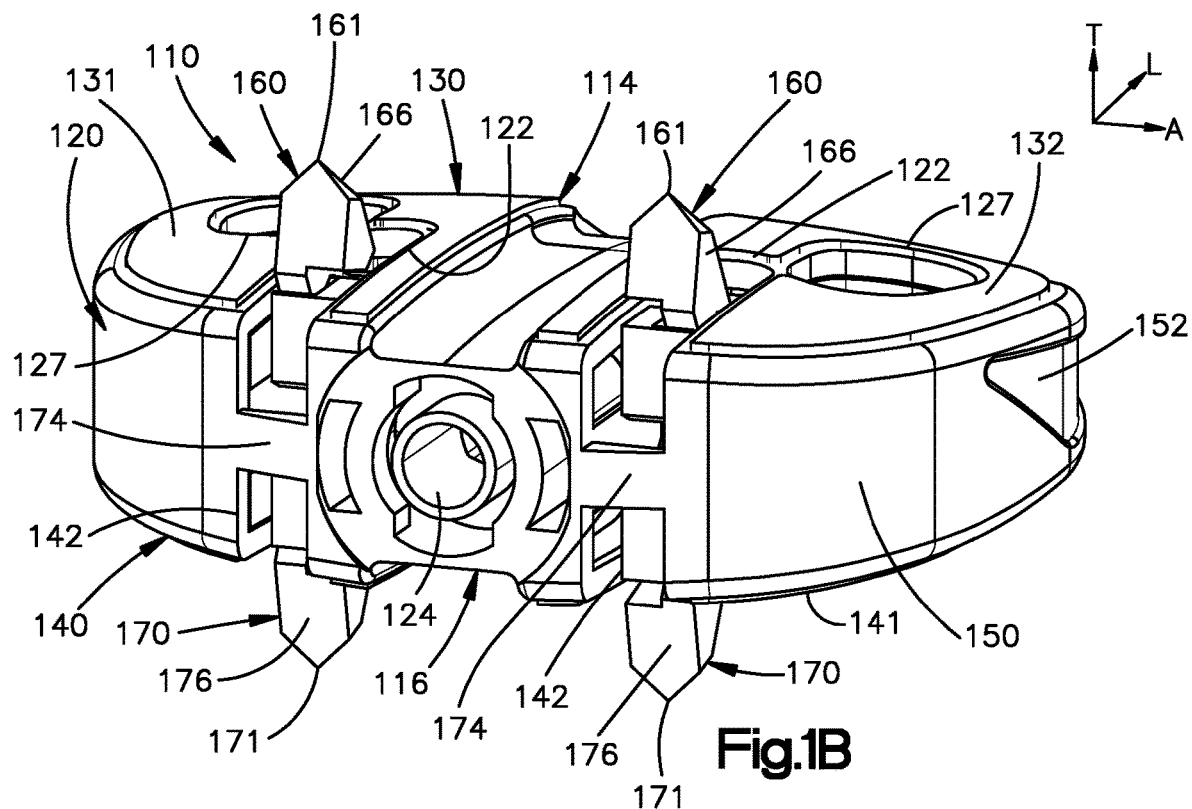
FIG. 1B is a perspective view of the intervertebral cage illustrated in FIG. 1A, showing deployable anchors in a deployed state.

Referring now to FIGS. 1A and 1B, an example of an intervertebral implant or cage 110 is configured for insertion into an intervertebral disc space. The intervertebral cage 110 can have an implant or cage body 120 that, in turn, includes an upper plate 130 and a lower plate 140 configured for placement against endplates of a pair of adjacent vertebral bodies that define the intervertebral disc space. The upper and lower plates 130 and 140, respectively, can be opposite each other along a transverse direction T. The upper plate 130 can be said to be spaced from the lower plate 140 in an upward direction. Similarly, the lower plate 140 can be said to be spaced from the upper plate 130 in a downward direction. Thus, the upward direction and the downward direction can define select directions that are oriented along the transverse direction T. The terms "up," "upward," and words of similar import can refer to the upward direction as used herein. The terms "down," "downward," and words of similar import can refer to the downward direction as used herein. The upper plate 130 can define an upper bearing surface 131 that is configured to bear against an endplate of a superior vertebral body when the intervertebral cage 110 is disposed in the intervertebral disc space. The lower plate 140 can define a lower bearing surface 141 that is configured to bear against an endplate of an inferior vertebral body when the intervertebral cage 110 is disposed in the intervertebral disc space.

The intervertebral cage 110 can define a first, leading end 114 with respect to insertion into the intervertebral disc space defined between the superior and inferior vertebrae. The intervertebral cage 110 can further define a second, trailing end 116 opposite the leading end 114 along a longitudinal direction L. The leading end 114 can be tapered to facilitate insertion into the intervertebral disc space. The longitudinal direction L can be oriented perpendicular to the transverse direction T. Thus, the intervertebral cage 110 can define a leading direction that extends from the trailing end 116 toward the leading end 114. Thus, leading components of the intervertebral cage 110 can be spaced from trailing components of the intervertebral cage in the leading direction. The intervertebral cage 110 can similarly define a trailing direction that extends from the leading end 114 toward the trailing end 116.

The body 120 can further include a sidewall 150 that is connected between the upper plate 130 and the lower plate. As shown, the upper and lower plates 130 and 140 can include a porous structure 132. The porous structure 132 can define at least a portion up to an entirety of one or both of the upper bearing surface 131 and the lower bearing surface 141. Similarly, the sidewall 150 can include a porous structure 152. The porous structures 132 and 152 can be configured to facilitate cellular activity and bony ingrowth from the adjacent vertebral bodies.

The intervertebral cage 110 can further include one or more deployable first or upper anchors 160 that are configured to penetrate and extend into the superior vertebral body. In one example, the intervertebral cage 110 can include a pair of upper anchors 160. The upper anchors 160 of the pair of upper anchors 160 can be spaced from each other along a lateral direction A that is perpendicular to each of the transverse direction T and the longitudinal direction L. Further, the upper anchors 160 can be aligned with each other along the lateral direction A. The upper anchors 160 can define a first or insertion position shown in FIG. 1A, whereby the anchors 160 are embedded in the cage body 120, such as the upper plate 130. The anchors 160 can be actuated or deployed to a second or deployed position shown in FIG. 1B, whereby the anchors 160 project through the upper plate 130 and out from the upper bearing surface 131.

The upper plate 130 can define one or more first or upper retention slots 122 that are configured to retain a respective one or more of the upper anchors 160. The upper anchors 160 can ride in the retention slots 122 as they travel between the first or insertion position and the second or deployed position. When the intervertebral cage 110 is disposed in the intervertebral space and the anchors 160 are in the deployed position, the anchors 160 can become embedded in the superior vertebral body. The upper anchors 160 can have at their respective distal ends a jutting upper protrusion or tooth 166 that extends out from the upper bearing surface 131 when the anchors 160 are in the second engaged position. The upper tooth 166 can have a sharp, bone-piercing upper edge or tip 161 that is configured to assist in piercing the superior vertebral body so as to embed the anchors 160 in the superior vertebral body.

The intervertebral cage 110 can be configured such that when the anchors 160 are in the first or insertion position, no portion of the anchors 160 extends beyond the upper bearing surface 131 along to the transverse direction T. Alternatively, the tip 161 can extend slightly beyond the upper bearing surface 131 when the anchors 160 are in the first or insertion position if, for instance, it is desired to roughen the endplate surface of the superior vertebral body during insertion of the intervertebral cage. As will be appreciated from the description below, the upper anchors 160 can be configured to be deployed simultaneously in one example.

The intervertebral cage 110 can further include one or more deployable second or lower anchors 170 that are configured to penetrate and extend into the superior vertebral body. In one example, the cage 110 can include an equal number of upper anchors 160 as lower anchors 170. For instance, the intervertebral cage 110 can include a pair of lower anchors 170. The lower anchors 170 of the pair of lower anchors 170 can be spaced from each other along the lateral direction A. The lower anchors 170 can be aligned with each other along the lateral direction A. Further, the lower anchors 170 can be aligned with respective ones of the upper anchors 160 along the transverse direction T. The lower anchors 170 can define a first or insertion position shown in FIG. 1A, whereby the lower anchors 170 are embedded in the cage body 120, such as the lower plate 140. The lower anchors 170 can be actuated or deployed to a second or deployed position shown in FIG. 1B, whereby the lower anchors 170 project through the lower plat 140 and out from the lower bearing surface 141.

The lower plate 140 can define one or more second or lower retention slots 142 that are configured to retain a respective one or more of the lower anchors 170. The lower anchors 170 can ride in the retention slots 142 as they travel between the first or insertion position and the second or deployed position. When the intervertebral cage 110 is disposed in the intervertebral space and the lower anchors 170 are in the deployed position, the lower anchors 170 can become embedded in the superior vertebral body. The lower anchors 170 can have at their respective distal ends a jutting lower protrusion or tooth 176 that extends out from the lower bearing surface 141 when the lower anchors 170 are in the second engaged position. The tooth 176 can have a sharp, bone-piercing edge or tip 171 that is configured to assist in piercing the inferior vertebral body so as to embed the anchors 170 in the inferior vertebral body.

It should be appreciated that the geometry of the teeth 166 and 176 can vary as desired. In one example, the sides of the teeth 166 and 176 can be smooth in one example. In another example, the sides of the teeth 166 and 176 can be barbed to assist with fixation in the vertebral body. Further, the respective tips 161 and 171 can be blunt or sharp as desired.

The intervertebral cage 110 can be configured such that when the lower anchors 170 are in the first or insertion position, no portion of the lower anchors 170 extends beyond the lower bearing surface 141 along to the transverse direction T. Alternatively, the tip 171 can extend slightly beyond the lower bearing surface 141 when the lower anchors 170 are in the first or insertion position if, for instance, it is desired to roughen the endplate surface of the superior vertebral body during insertion of the intervertebral cage. As will be appreciated from the description below, the lower anchors 170 can be configured to be deployed simultaneously in one example.

When the upper and lower anchors 160 and 170 are in their first or insertion position, the cage 110 can be said to be in the first or insertion configuration. The cage 110 can be configured to simultaneously deploy the upper anchors 160 and the lower anchors 170.

Figure 2A:
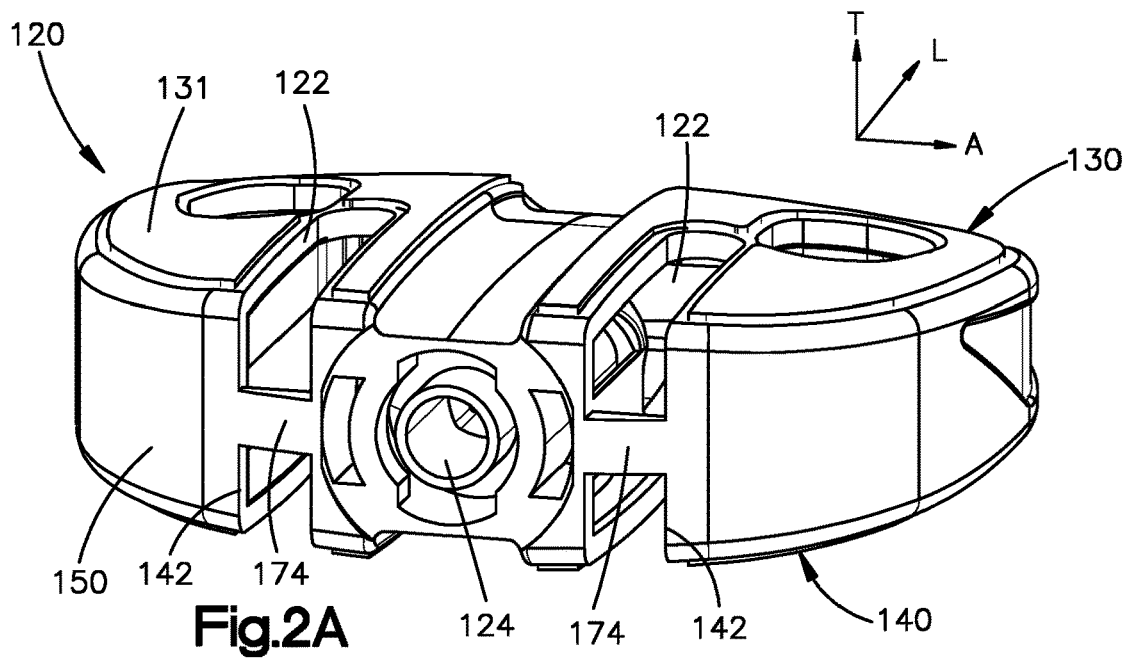
FIG. 2A is a perspective view of a body of the intervertebral cage illustrated in FIG. 1A.
Figure 2B:
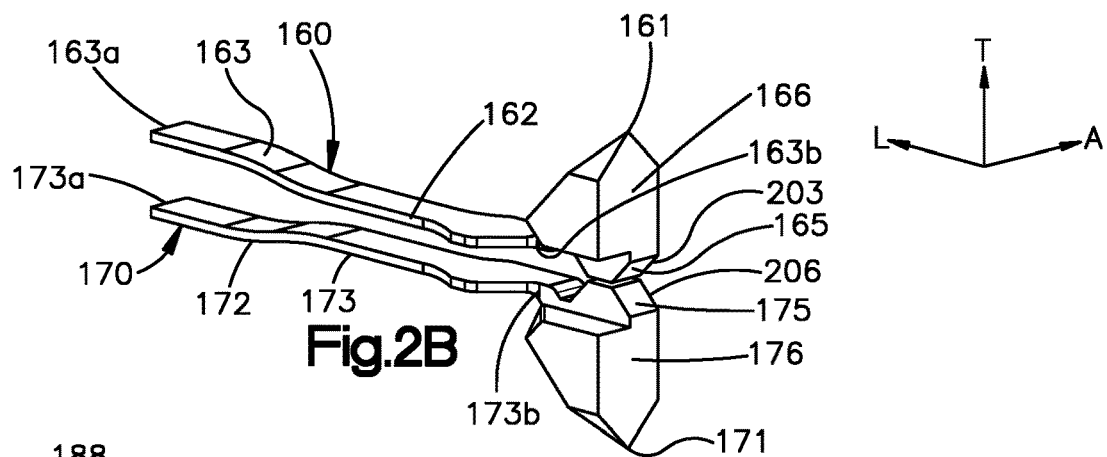
FIG. 2B is a perspective view of upper and lower anchors of the intervertebral cage illustrated in FIG. 1A.
Figure 2C:
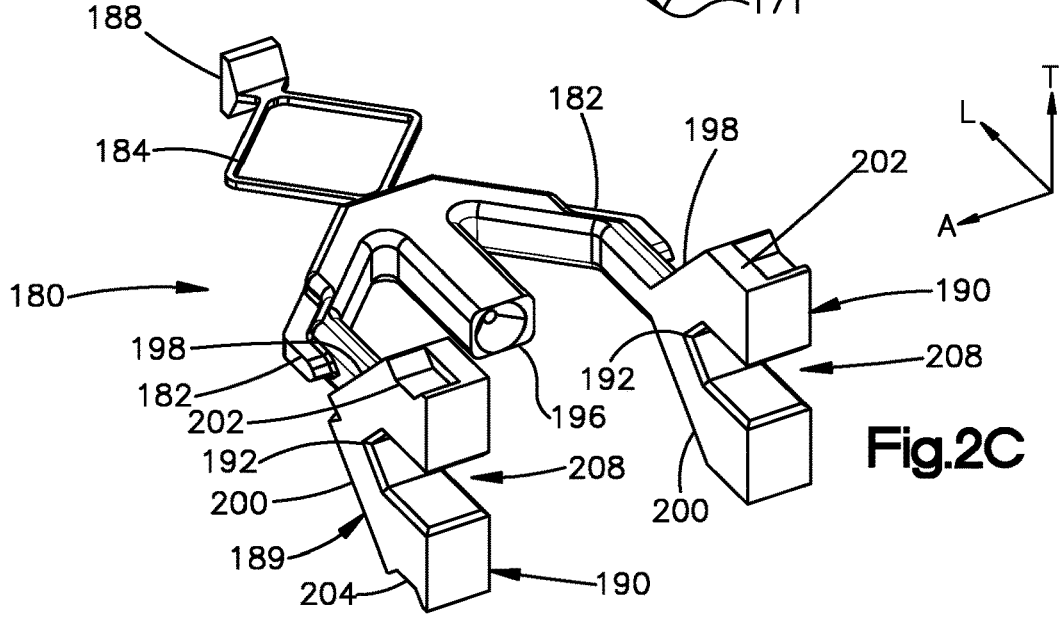
FIG. 2C is a perspective view of an actuator of the intervertebral cage illustrated in FIG. 1A.
Figure 3:
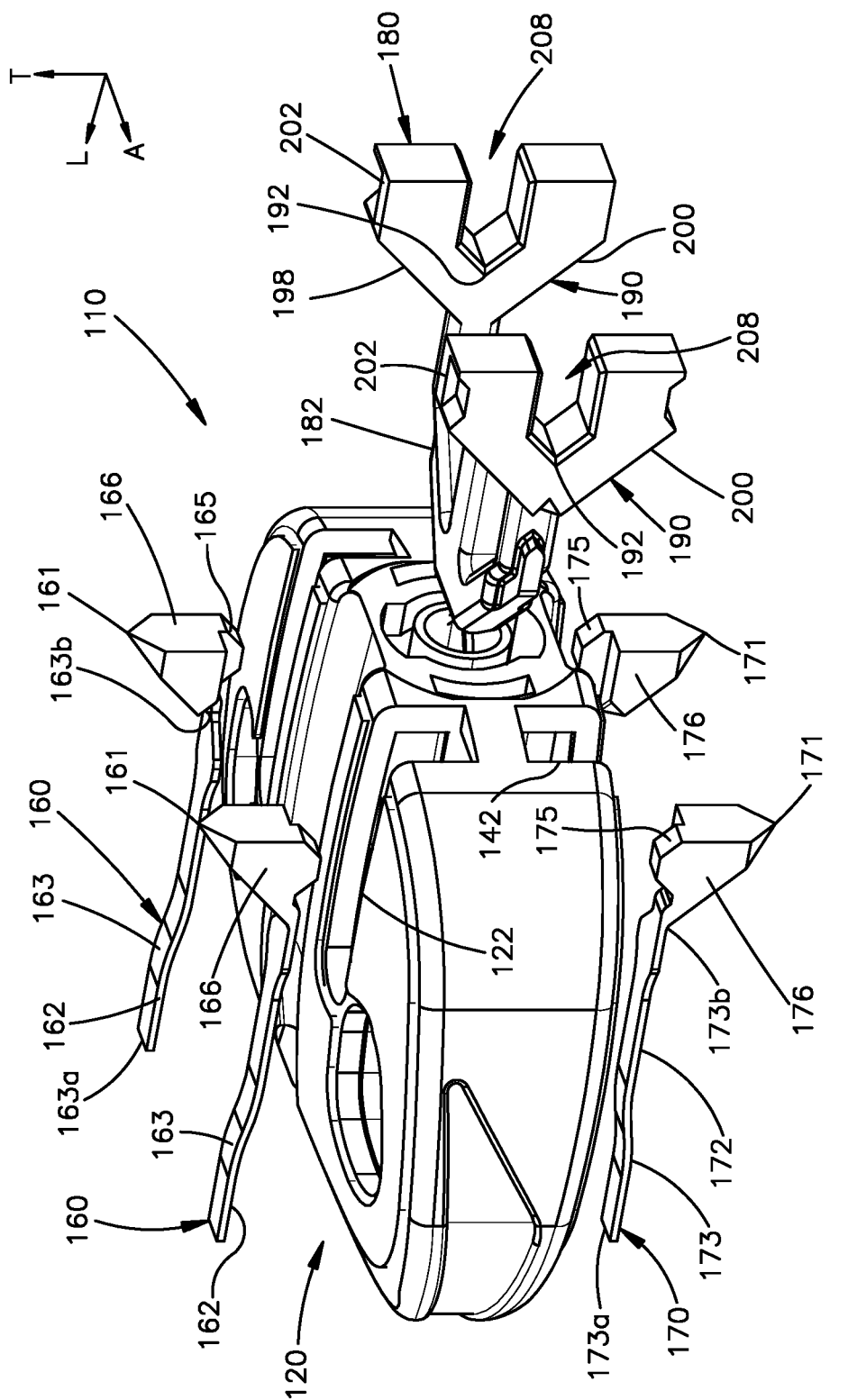
FIG. 3 is an exploded perspective view of the intervertebral cage illustrated in FIG. 1A.
Figure 4:
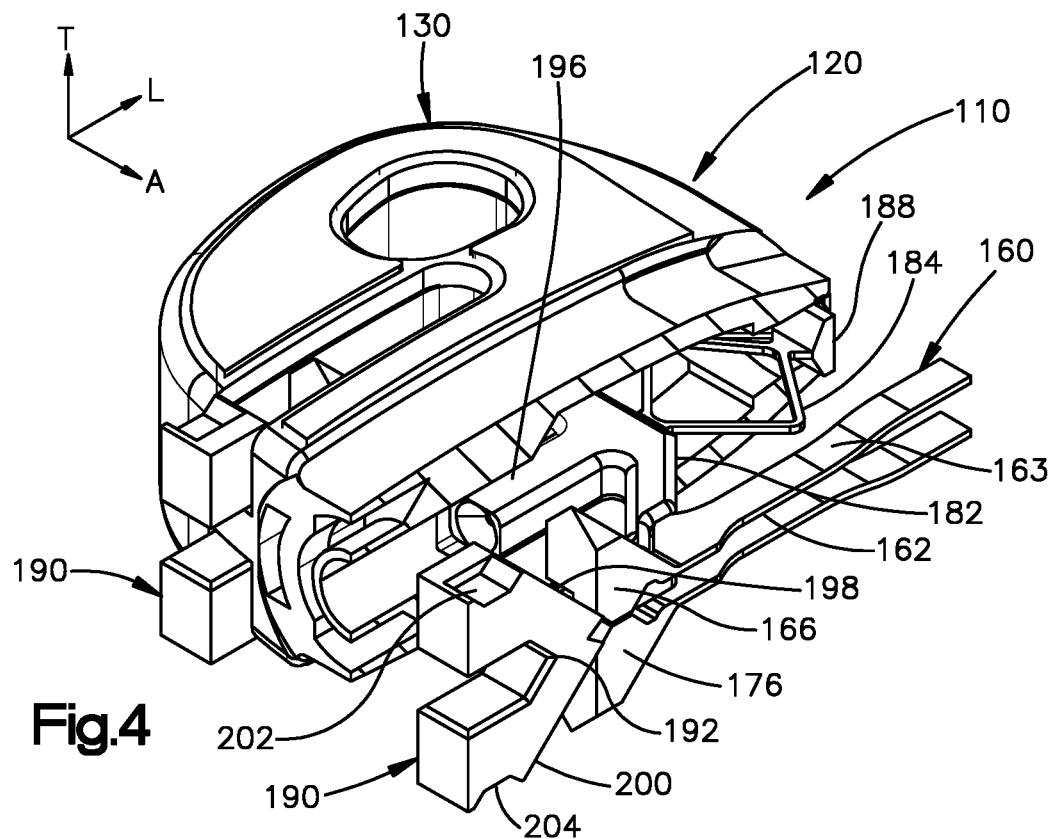
FIG. 4 is a cross-sectional view of the intervertebral cage illustrated in FIG. 1B, with portions removed for the purposes of clarity, shown when the cage is in the initial or insertion configuration.
Figure 5:
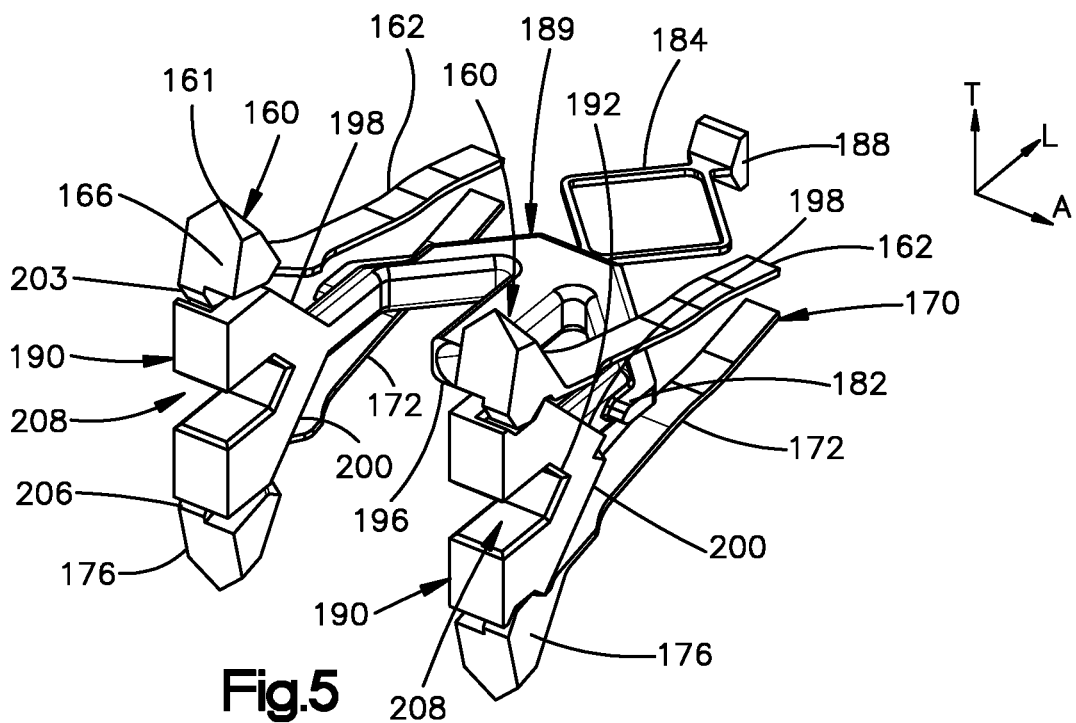
FIG. 5 is a perspective view of the actuator and anchors of the intervertebral cage illustrated in FIGS. 2B and 2C, shown with the anchors in a deployed position.

Referring now to FIGS. 2A-3, each of the upper anchors 160 can further include an upper spring member 162, such that the upper tooth 166 extends out from the spring member 162. The upper tooth 166 can fixedly extend out from the spring member 162, such that the upper tooth 166 is not movable with respect to the spring member 162, in some examples. The spring member 162 can provide a spring force that biases the upper tooth 166 toward the insertion position. In one example, the upper spring member 162 can be configured as an upper cantilever spring 163. A first end 163a of the upper cantilever spring 163 can be secured to the body 120 at a securement location. The upper tooth 166 can extend from the cantilever spring 163 at a location spaced from the first end. For instance, the upper tooth 166 can extend from a second end 163b of the cantilever spring 163 that is opposite the first end. In one example, the cantilever spring 163 can be oriented along the longitudinal direction. Thus, the first end 163a can be front end of the cantilever spring 163, and the second end 163b can be a rear end of the cantilever spring 163. Thus, the cantilever spring 163 can extend rearward from the securement location to the upper tooth 166. Alternatively, the first end 163a can be a rear end of the upper cantilever spring 163, and the second end 163b can be a front end of the upper cantilever spring 163. Alternatively still, the cantilevered spring 163 can be oriented in any alternative direction as desired. It should be further appreciated, of course, that the spring member 162 can be alternatively constructed in any suitable manner as desired. For instance, the spring member 162 can be configured as a coil spring, a leaf spring, or any suitable alternative spring as desired.

It should be further appreciated that the upper anchors 160 can include one or more teeth 166 that extend out from the spring member 162 and move between the insertion position and the deployed position together. Alternatively, the cage 110 can include a plurality of upper anchors 160 that are arranged as desired. For instance, the cage 110 can include multiple rows of upper anchors 160. The rows can be oriented along the central axis of the cantilevered spring member, and spaced from each other along the lateral direction A.

With continuing reference to FIGS. 2A-3, each of the lower anchors 170 can further include a lower spring member 172, such that the lower tooth 176 extends out from the spring member 172. The lower tooth 176 can fixedly extend out from the spring member 172, such that the lower tooth 176 is not movable with respect to the spring member 172, in some examples. The spring member 172 can provide a spring force that biases the lower tooth 176 toward the insertion position. In one example, the lower spring member 172 can be configured as a lower cantilever spring 173. A first end 173a of the lower cantilever spring 173 can be secured to the body 120 at a securement location. The lower tooth 176 can extend from the cantilever spring 173 at a location spaced from the first end. For instance, the lower tooth 176 can extend from a second end 173b of the cantilever spring 173 that is opposite the first end. In one example, the cantilever spring 173 can be oriented along the longitudinal direction. Thus, the first end 173a can be front end of the cantilever spring 173, and the second end 173b can be a rear end of the cantilever spring 173. Thus, the cantilever spring 173 can extend rearward from the securement location to the lower tooth 176. Alternatively, the first end 173a can be a rear end of the lower cantilever spring 173, and the second end 173b can be a front end of the lower cantilever spring 173. Alternatively still, the cantilevered spring 173 can be oriented in any alternative direction as desired. It should be further appreciated, of course, that the spring member 172 can be alternatively constructed in any suitable manner as desired. For instance, the spring member 172 can be configured as a coil spring, a leaf spring, or any suitable alternative spring as desired.

It should be further appreciated that the lower anchors 170 can include one or more teeth 176 that extend out from the spring member 172 and move between the insertion position and the deployed position together. Alternatively, the cage 110 can include a plurality of lower anchors 170 that are arranged as desired. For instance, the cage 110 can include multiple rows of lower anchors 170. The rows can be oriented along the central axis of the cantilevered spring member, and spaced from each other along the lateral direction A. In one example, the upper anchors 160 and the lower anchors 170 can be mirror images of each other about a plane that is oriented along the longitudinal direction L and the lateral direction A.

Referring now to FIG. 2C, the cage 110 can further include an actuator 180 that is supported in the body 120, and movable in an actuation direction to deploy the anchors 160 and 170. The actuator 180 is movable from a first or initial position in the actuation direction to a second or actuated position. Movement of the actuator 180 in the actuation direction can be a translation along a straight linear direction. When the actuator 180 is in the initial position, the anchors 160 and 170 can be in their insertion positions. As the actuator 180 is moved from the initial position to the actuated position, the actuator 180 urges the anchors 160 and 170 to their deployed positions. The cage body 120, the actuator 180, and the anchors 160 and 170 can be manufactured together so as to form a single complete construct, as described above.

The actuator 180 can include a first end that can include stop member 188, a second end that can include a plunger mechanism 189 opposite the stop member 188, and an actuator spring 184 that is connected between the stop member 188 and the plunger mechanism 189. The actuator spring 184 can define a compression spring that is compressible along the longitudinal direction so as to apply a counter biasing force. At least a portion of the actuator 180 is configured to be disposed in an internal void 193 of the cage body 120 (see FIGS. 6A-6B). The stop member 188 is configured to bear against a seat surface of the cage body 120, and thus can be held stationary relative to the cage body 120 during operation. The seat surface of the cage body 120 can partially define the internal void 193. Alternatively, the stop member 188 can be monolithic with the cage body 120. The actuator spring 184 is configured to apply a spring force as the plunger mechanism 189 travels toward the stop member 188. In particular, the spring force urges the plunger mechanism 189 away from the stop member 188 as the plunger mechanism 189 travels toward the stop member 188 in the actuation direction.

The actuator 180 can be oriented in the cage body 120 such that the first end is spaced from the plunger in the forward direction. Thus, the first end can define a front end, and the second end can define a rear end. The plunger mechanism 189 is therefore movable with respect to the first end in the forward direction. In particular, the plunger mechanism 189 can receive an actuation force that urges the plunger mechanism 189 to travel in the forward direction against the force of the actuator spring 184. The actuation force can be a push force in one example.

The plunger mechanism 189 can include an actuator shaft 196 that is configured to receive the actuation force. For instance, as shown in FIG. 2A, the cage body 120 can include a guide sleeve 124 that is aligned with the central axis of the actuator shaft 196. The guide sleeve 124 is therefore configured to receive a driver shaft of a driver instrument, and guide the driver shaft toward a bearing surface 197 of the actuator shaft 196. As the driver shaft is further driven in the forward direction, the driver shaft applies a drive force to the actuator shaft 196, and thus to the plunger mechanism 189, that causes the plunger mechanism 189 to travel in the forward direction relative to the cage body 120 against the spring force of the actuator spring 184. Thus, after insertion of the intervertebral cage 120 into the intervertebral disc space, the anchors 160 may be deployed by first inserting a driver instrument that is configured to engage the actuator 180, and applying the drive force to the actuator 180 that drives the actuator 180 to travel in the actuation direction within the cage body 120. The guide sleeve 124 of the cage body 120 can be configured as a bayonet instrument interface, so that the opening defined by the guide sleeve 124 can serve multiple functions and allow the guide body 120 to be adapted for use with other instruments and devices. The drive force can be applied in the forward direction in one example. Thus, the actuation direction can be defined by the forward direction.

Alternatively, the actuator 180 can be oriented in the cage body such that the first end is spaced from the plunger in the rearward direction. Thus, the first end can define a rear end, and the second end can define a front end. The plunger mechanism 189 would therefore be movable with respect to the first end in the rearward direction. In particular, the plunger mechanism 189 can receive an actuation force that urges the plunger mechanism 189 to travel in the rearward direction against the force of the actuator spring 184. The actuation force can be a pull force in this alternative example. Thus, the drive force can be applied to the plunger mechanism 189 in the rearward direction. Thus, the actuation direction can be defined by the rearward direction.

The plunger mechanism 189 can include at least one ramp 190 that is configured to engage a respective at least one of the anchors 160 and 170 so as to urge the at least one anchor from the insertion position to the deployed position as the plunger mechanism, and thus the at least one ramp, travels in the actuation direction to the actuated position. In one example, the plunger mechanism 189 can include first and second ramps 190 that are configured to engage respective different ones of the anchors 160 and 170. The first and second ramps 190 can travel parallel to each other along the actuation direction. In one example, the actuator shaft 196 can be disposed between the ramps 190 with respect to the lateral direction A. For instance, the actuator shaft 196 can be aligned with the ramps 190 along the lateral direction A. Further, each of the first and second ramps 190 can include one or both of a first or upper ramped surface 198 and a second or lower ramped surface 200. The upper ramped surface 198 and the lower ramped surface 200 can thus be monolithic with each other. The upper ramped surface 198 and the lower ramped surface 200 can be aligned with each other along the transverse direction. The upper ramped surface 198 can be sloped upward as it extends rearwardly opposite the direction of the drive force. The lower ramped surface 200 can be sloped downward as it extends rearwardly opposite the direction of the drive force.

The ramps 190 can be supported relative to the actuator shaft 196, such that the ramps 190 travel along with the actuator shaft 196. Thus, as the actuator shaft 196 is driven in the forward direction in response to the drive force, the ramps 190 likewise travel in the forward direction. In one example, the plunger mechanism 189 can include first and second arms 182 that can flare laterally outward from the actuator shaft 196 and rearward, and can support the ramps 190. The first and second arms 182 can be cantilevered from the actuator shaft 196 in one example. The ramps 190 can be aligned with each other along the lateral direction, or can be alternatively positioned as desired.

Referring now to FIGS. 2B-2C and FIGS. 4-6B, when the actuator 180 is in the initial position, the upper and lower ramped surfaces 198 and 200 are aligned with respective bearing surfaces 165 and 175 of the upper and lower anchors 160 and 170 in the actuation direction. For instance, the ramp 190 can define a tapered tip that is aligned with a gap between the bearing surfaces 165 and 175 in the actuation direction. The ramped surfaces 198 and 200 can extend rearwardly from the tapered tip. The upper bearing surface 165 can be defined by a surface of the upper tooth 166. The upper bearing surface 165 can also define a ramped surface. For instance, the upper bearing surface 165 can be sloped upward as it extends rearwardly. Thus, the upper bearing surface 165 can be parallel to the upper ramped surface 198. Similarly, the lower bearing surface 175 can be defined by a surface of the lower tooth 176. The lower bearing surface 175 can also define a ramped surface. For instance, the lower bearing surface 175 can be sloped downward as it extends rearwardly. Thus, the lower bearing surface 175 can be parallel to the lower ramped surface 200.

During operation, as the actuator 180, and in particular the plunger mechanism 189, and more particularly still the at least one ramp 190, is driven in the actuation direction, the upper bearing surface 165 rides along the upper ramped surface 198. The slope of the upper ramped surface 198 urges the corresponding upper tooth 166 outward along the transverse direction T against the force of the upper spring member 162 to the deployed position. In this regard, it should be appreciated that the upper spring member 162 biases the upper tooth 166 into contact with the upper ramped surface 198. Similarly, the lower bearing surface 175 rides along the lower ramped surface 200. The slope of the lower ramped surface 200 urges the corresponding lower tooth 176 outward along the transverse direction T against the force of the lower spring member 172 to the deployed position. In this regard, it should be appreciated that the lower spring member 172 biases the lower tooth 176 into contact with the lower ramped surface 200.

It should be appreciated that the upper and lower bearing surfaces 165 and 175 can thus be sloped equally and opposite each other. Further, the upper and lower ramped surfaces 198 and 200 can be sloped equally and opposite each other. Alternatively, the upper and lower ramped surfaces 198 and 200 can be sloped opposite each other and at different slopes if it is desired to insert the upper and lower anchors 160 and 170 into the respective superior and inferior vertebrae at different depths.

With continuing reference to FIGS. 4-6B, each of the ramps 190 can be configured to intermesh or releasably interlock with the respective one or both of the upper anchor 160 and the lower anchor 170 when the anchors 160 and 170 are in their deployed position. In particular, at least one of the ramps 190 up to all of the ramps 190 can define an upper retention pocket 202 that is configured to receive a portion of the upper anchor 160. The upper retention pocket 202 can be spaced from the upper ramped surface 198 in the rearward direction. In one example, the upper retention pocket 202 can extend downward into a flat surface that extends rearwardly from the upper ramped surface. The flat surface can be substantially planar along the lateral direction L and the longitudinal direction L. A transverse inner, or lower, end of the upper tooth 166 can define a projection 203 that is sized to be received in the retention pocket 202. The projection 203 can further define the upper bearing surface 165. Similarly, at least one of the ramps 190 up to all of the ramps 190 can define a lower retention pocket 204 that is configured to receive a portion of the lower anchor 170. The lower retention pocket 204 can be spaced from the lower ramped surface 200 in the rearward direction. In one example, the lower retention pocket 204 can extend upwards into a flat surface that extends rearwardly from the upper ramped surface. The flat surface can be substantially planar along the lateral direction L and the longitudinal direction L. A transverse inner, or upper, end of the lower tooth 176 can define a projection 206 that is sized to be received in the retention pocket 204. The projection 206 can further define the lower bearing surface 175.

During operation, the upper tooth 166 rides along the upper ramped surface 198 until it is fully deployed. Continued travel of the ramp 190 in the forward direction, for instance as the plunger mechanism 189 travels in the forward direction, causes the upper tooth to continue to ride along the ramp 190 until the projection 203 is received in the corresponding upper retention pocket 202. Similarly, during operation, the lower tooth 176 rides along the lower ramped surface 200 until it is fully deployed. Continued travel of the ramp 190 in the forward direction, for instance as the plunger mechanism 189 travels in the forward direction, causes the lower tooth 176 to continue to ride along the ramp 190 until the projection 206 is received in the corresponding lower retention pocket 204.

The spring force of the upper spring member 162 can apply a retention force to upper tooth 166 that retains the upper tooth 166, and in particular the projection 203, in the upper retention pocket 202. Similarly, the spring force of the lower spring member 172 can apply a retention force to lower tooth 176 that retains the lower tooth 176, and in particular the projection 206, in the lower retention pocket 204. The retention force applied by the spring members 162 and 172 is further sufficient to prevent the spring force of the actuator spring 184 from driving the plunger mechanism 189, and thus the ramp 190, to move in the rearward direction, which would cause the anchors 160 and 170 to return to the insertion position. Otherwise stated, the retention force applied by the spring members 162 and 172, alone or in combination, can be sufficient to retain the actuator 180 in the actuated position. The ramp 190 can be disposed in the cage body 120 when the actuator 180 is in the actuated position. In some examples, a portion of the ramp 190 can extend out from the cage body 120 when the actuator is in the initial position.

Thus, the upper and lower teeth 160 and 170 are thus locked securely to the ramp 190, which allows the teeth 160 and 170 to pierce and extend into the respective vertebral body, thereby allowing the intervertebral cage 110 to have better fixation to bone, while preventing the embedded anchors 160 and 170 from interfering with the insertion process when the anchors 160 and 170 are in their insertion position. While the ramp 190 can define pockets and the anchors 160 and 170, and in particular the teeth 166 and 176 can be received in the pockets, it should be appreciated that the anchors 160 and 170, and in particular the teeth 166 and 176, can define the pockets, and the ramp 190 can have protrusions that are received in the pockets. Thus, one of the ramp 190 and the upper anchor 160 can define a pocket, and the other of the ramp 190 and the upper anchor 160 can be configured to be received in the pocket after the upper anchor 160 has been moved to its deployed position. Further, one of the ramp 190 and the lower anchor 170 can define a pocket, and the other of the ramp 190 and the lower anchor 170 can be configured to be received in the pocket after the lower anchor 170 has been moved to its deployed position.

Referring now to FIG. 1A and FIG. 3, the actuator 180 can be captured in the cage body 120 as it moves from its initial position to its actuated position. In particular, the stop member 188 can abut the cage body 120 or be monolithic with the cage body 120 at the first end of the actuator 180 (collectively referred to herein as "engaging" the cage body 120. The second end of the actuator 180 can also bear against the cage body 120. For instance, the plunger mechanism 189 can include a brace member 192 that is configured to abut at least one brace member 174 of the cage body 120. In particular, the brace member 192 can be disposed forward of the brace member 174 of the cage body 120. Further, the actuator 180 can be spaced such that when the stop member 188 is engaged with the cage body 120, and the brace members 174 and 192 abut each other, the actuator spring 184 can be compressed. Thus, the actuator 180 can be captured in the cage between the seat surface of the cage body 120 and the brace member 174 of the cage body. The actuator spring 184 can exert a biasing force that can urge the stop member 188 against the seat surface of the cage body 120, and further exerts a biasing force that urges the brace member 192 of the actuator 180 against the brace member 174 of the cage body 120.

In one example, the actuator 180 can define a guide slot 208 that receives the brace member 174 of the cage body 120. The guide slot 208 can terminate longitudinally at the brace member 192 of the actuator 180. Thus, the brace member 174 can extend into the slot and abut the brace member 192 when the actuator is in the initial position. As the actuator 180 is moved to the actuated position, the brace member 192 of the actuator 180 moves forward, or in the actuation direction, with respect to the brace member 174 of the cage body 120. It should be appreciated that the term "forward," "front," and derivatives thereof can refer equally to the actuation direction. However, in alternative embodiments as described above, the actuation direction can alternatively be oriented in the rearward direction.

However, the brace member 174 can remain in the guide slot 208 when actuator 180 is in the actuated position. Alternatively, the brace member 174 can be removed from the guide slot 208, and rearwardly spaced from the open rear end of the guide slot 208, when the actuator 180 is in the actuated position. In one example, the actuator 180 can include at least one guide slot 208 that extends forward into a rear end of the at least one of the ramps 190. The brace member 192 of the actuator 180 can thus be defined by the surface of the ramp 190 that defines the front end of the guide slot 208. The guide slot 208 can be disposed between the upper ramped surface 198 and the lower ramped surface 200. In one example, the actuator 180 can include a guide slot 208 that extends into each of the ramps 190. Similarly, the cage body 120 can include a respective brace member 174 that is disposed in each of the guide slots 208. While the actuator 180 can define the at least one guide slot 208 and the cage body 120 can define the at least one brace member 174 that is disposed in the at least one guide slot 208, it should be appreciated that the cage body 120 can alternatively define the at least one guide slot 208, and the actuator 180 can alternatively define the at least one brace member 174 that is disposed in the at least one guide slot 208.

Figure 7A:
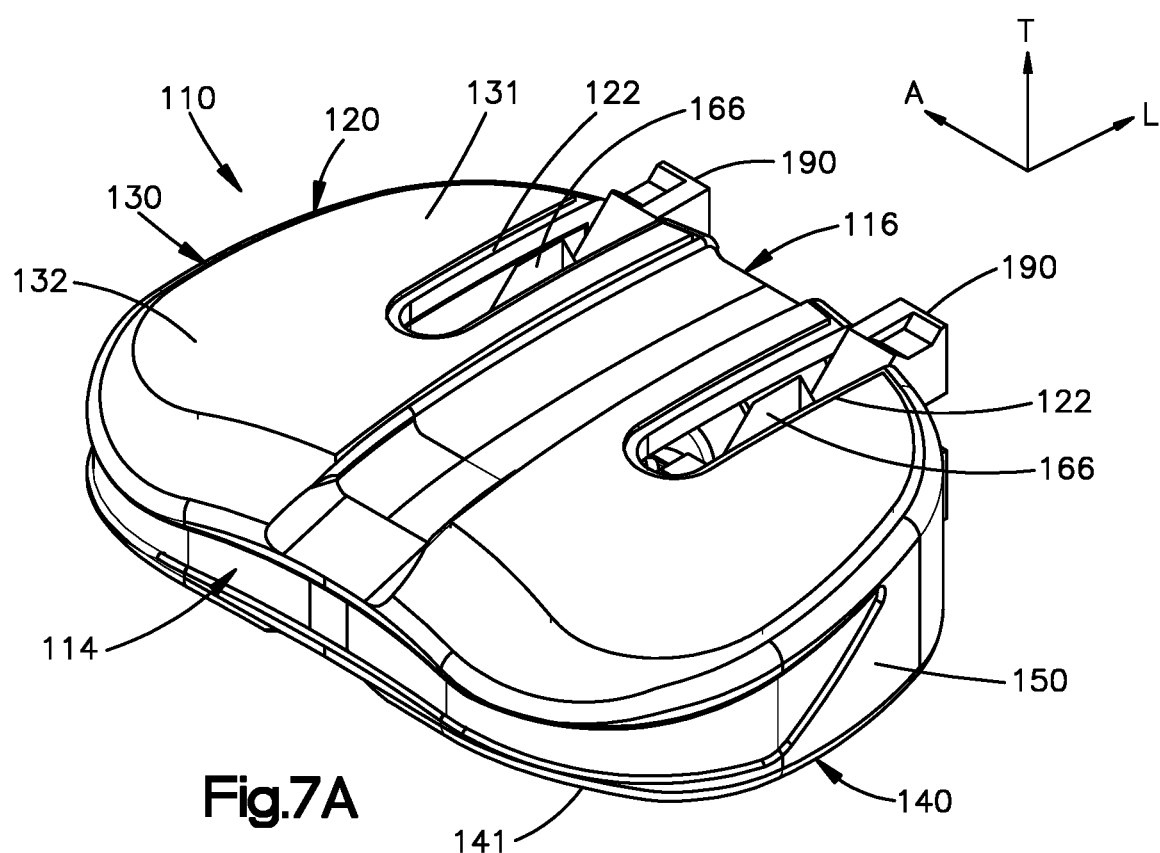
FIG. 7A is a perspective view of the intervertebral cage similar to the cage as illustrated in FIG. 1A, but shown without bone graft insertion holes.
Figure 7B:
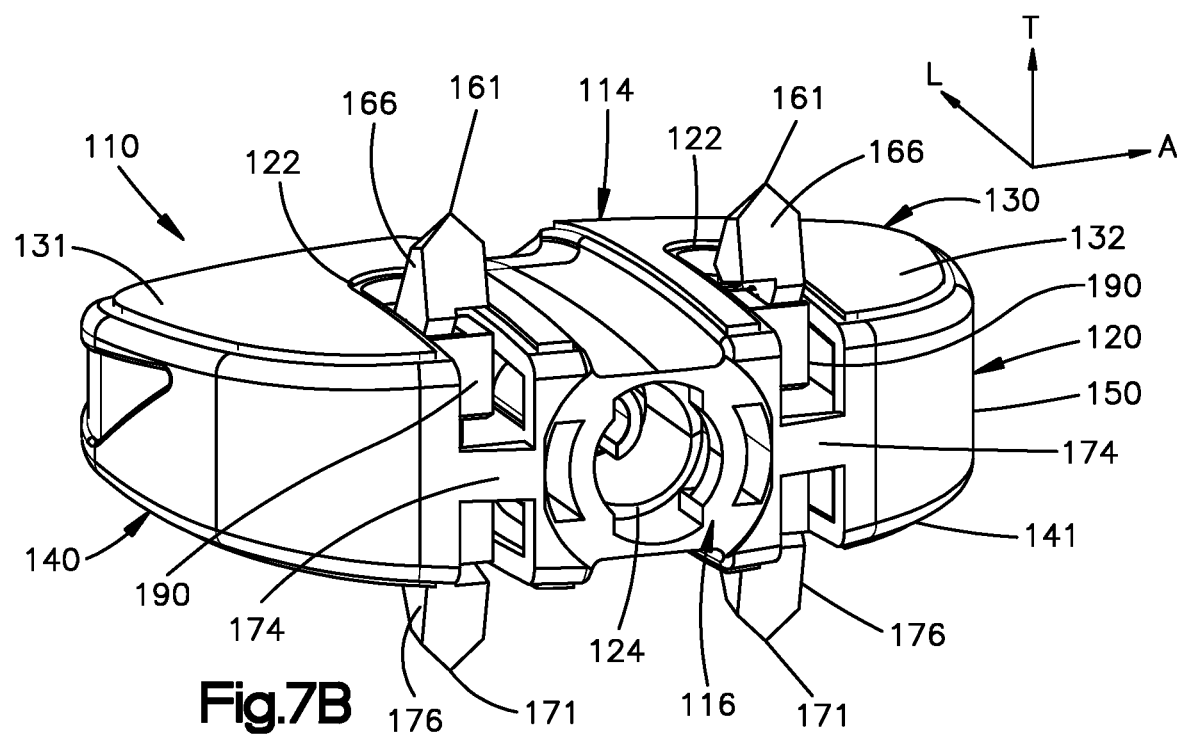
FIG. 7B is a perspective view of the intervertebral cage similar to the cage as illustrated in FIG. 1B, but shown without bone graft insertion holes.
Figure 8A:
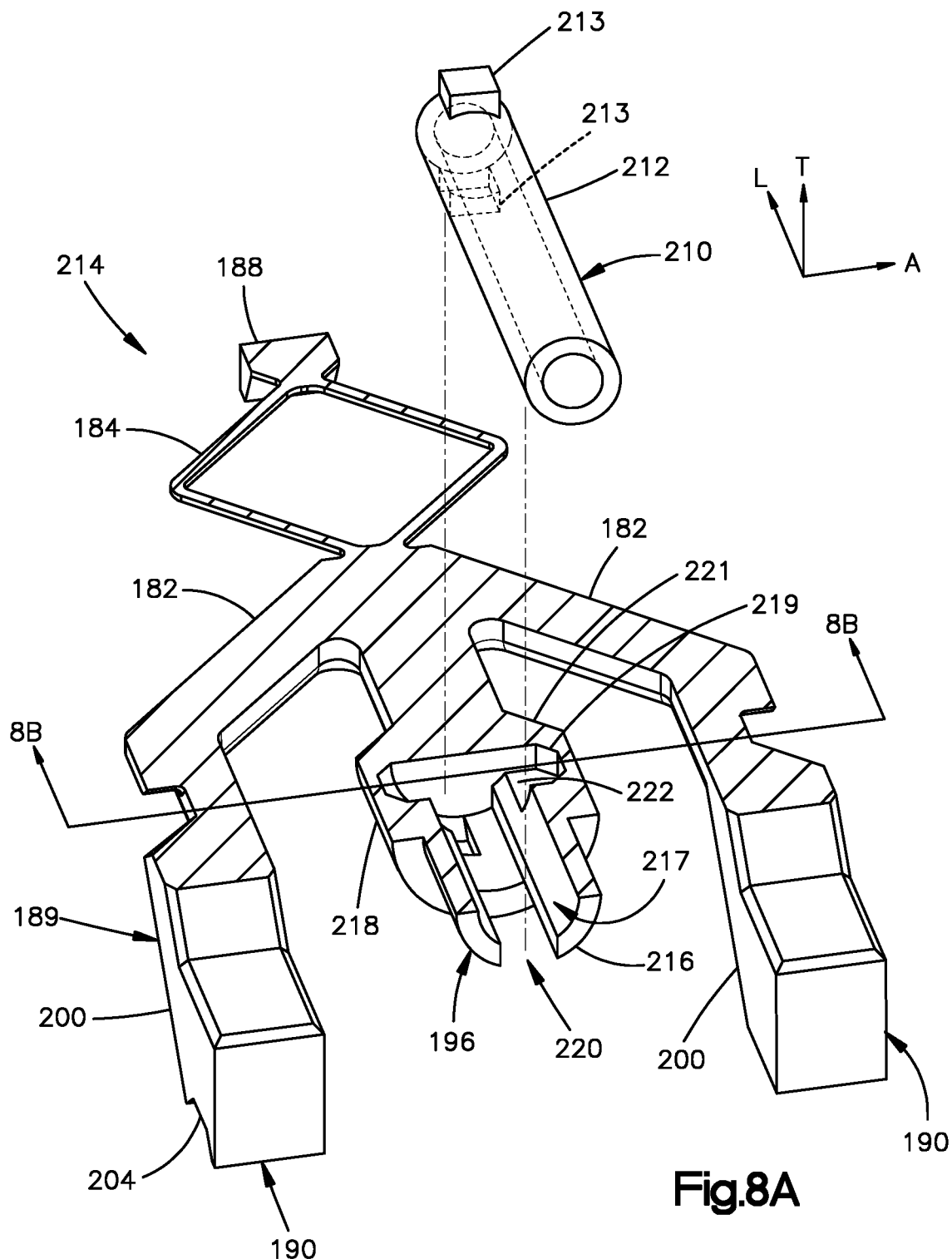
FIG. 8A is an exploded perspective view of an actuator of the intervertebral cage of FIG. 1B and a driver instrument, wherein the implant actuator is shown in cross-section.

Referring now again to FIG. 1A, the intervertebral cage 110 can include one or more bone graft insertion holes 127 that extend at least into or through the cage body 120 along the transverse direction T. For instance, the one or more bone graft insertion holes 127 can extend through the upper plate 130, the lower plate 140, or both the upper plate 130 and the lower plate 140 along the transverse direction. Bone graft can be inserted into the cage body 120 through the bone graft insertion holes 127 to promote bony ingrowth and fusion to the respective vertebral bodies. Alternatively, as illustrated in FIG. 7A-7B, the intervertebral cage of FIGS. 1A-1B is shown without bone graft insertion holes 127. In particular, the bone graft insertion holes has been replaced by the porous structure 132 described above. In one example, a portion up to an entirety of the bearing surfaces 131 and 141 can be defined by the porous structure 132.

Referring now to FIGS. 1A-1B and FIGS. 8A-8C, and as described above, a driver instrument 210 can be configured to drive the actuator in the actuation direction, thereby causing the ramp 190 to deploy at least one anchor, such as the upper anchor 160 and the lower anchor 170. In particular, the driver instrument 210 can include a driver shaft 212 that is configured to abut the actuator shaft 196, such that movement of the driver shaft 212 in the actuation direction drives the plunger mechanism 189, and thus the at least one ramp 190, in the actuation direction. It should thus be appreciated that an implant assembly 214 can include the cage 110 and the driver instrument 210.

Figure 6A:
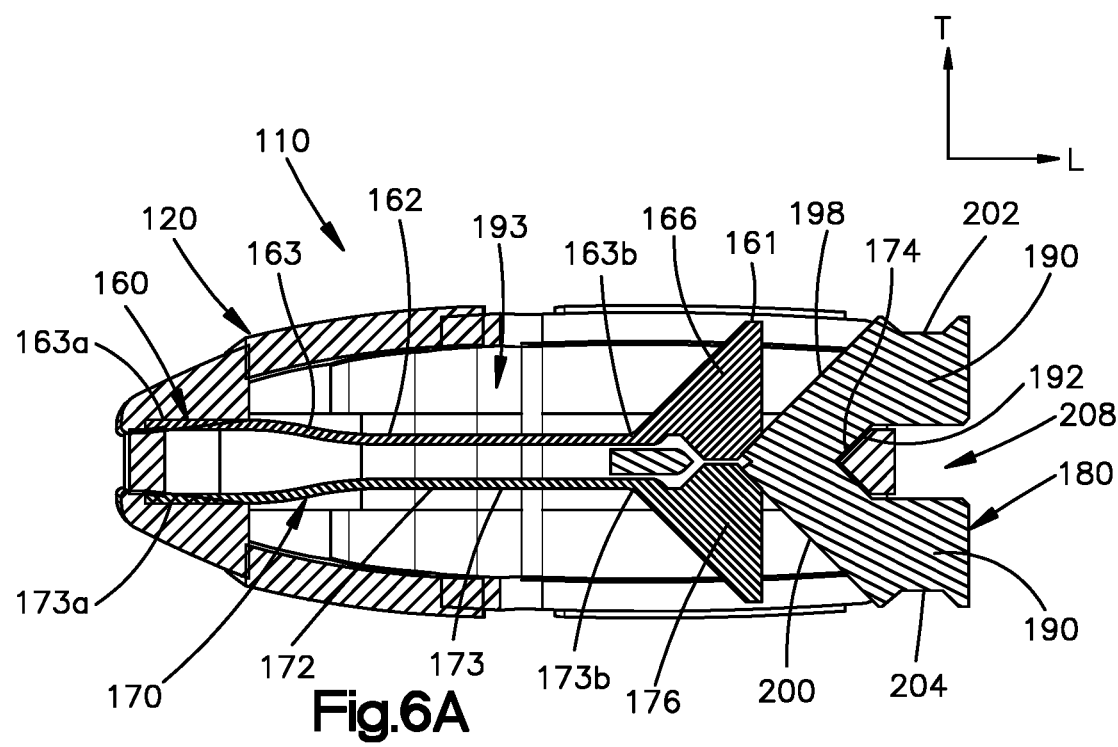
FIG. 6A is a sectional side elevation view of the intervertebral cage illustrated in FIG. 1A.
Figure 6B:
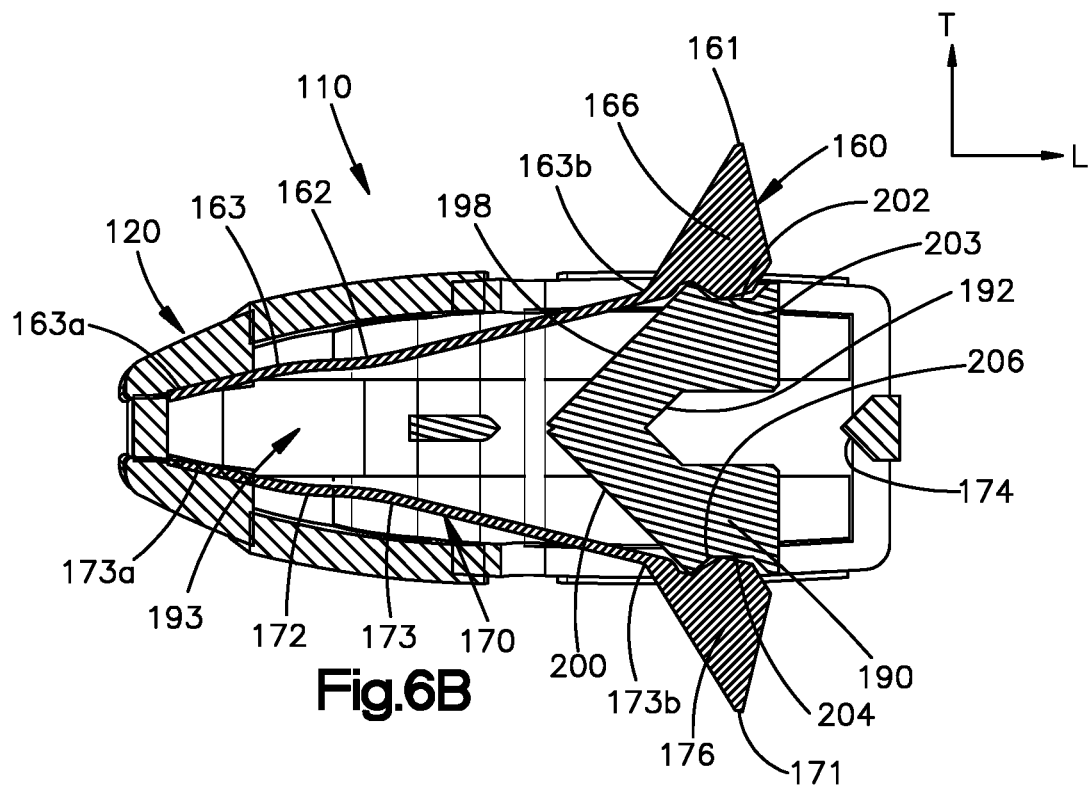
FIG. 6B is a sectional side elevation view of the intervertebral cage of FIG. 1B.

In some instances, it may be desirable to remove the intervertebral cage 110 from the intervertebral disc space after the anchors 160 and 170 have been deployed. Accordingly, it may be desirable to return the anchors 160 and 170 from the deployed position to the insertion position in order to allow for the removal of the intervertebral cage 110. The driver instrument 210 can be configured to drive the plunger mechanism 189, and thus the at least one ramp 190, in a reverse direction opposite the actuation direction. When the actuation direction is defined by the forward direction, the reverse direction can be defined by the rearward direction. In particular, the driver instrument 210 can be inserted into the cage 110 in the actuation direction to engage the actuator 180. The driver instrument 210 can then be moved in the reverse direction to correspondingly move the plunger mechanism 189, and thus the at least one ramp 190, in the reverse direction. As shown in FIGS. 6A-6B, as the ramp 190 moves in the reverse direction, the actuators the teeth 166 and 176 are removed from the corresponding pockets 202 and 204. Continued movement of the ramp 190 in the reverse direction causes the teeth 166 and 176 to ride along the ramped surfaces 198 and 200, respectively, which causes the teeth 166 and 176 to retract into the cage body 120 under the spring force of the spring members 162 and 172, respectively. Once the teeth 166 and 176 have been returned to the insertion position, the cage 110 can be removed from the intervertebral space.

The actuator shaft 196 can include an inner shaft portion 216 and an outer shaft portion 218 that is adjacent the inner shaft portion. For instance, the outer shaft portion can be disposed forward from the inner shaft portion 216. The inner shaft portion 216 can define a lumen 217 that is sized to receive the driver shaft 212 when the driver shaft 212 is in a first rotational position. The outer shaft portion 218 can define a void 219 that is open to the lumen of the inner shaft portion 216. The lumen 217 of the inner shaft portion 216 can define an inner cross-section that is smaller than an inner cross-section of the void 219 of the outer shaft portion 218. In one example, the lumen 217 and the void 219 can be circular in cross-section. The void 219 can be defined between the inner shaft portion 216 and a second shaft portion 221 that extends forward from the outer shaft portion 218.

In one example, the inner shaft portion 216 can be slotted. That is, the actuator shaft 196 can define at least one slot 220 that extends through a wall of the inner shaft portion 216 and into the lumen 217. The inner shaft portion 216 can define as many slots 220 as desired. In one example, the inner shaft portion 216 defines a pair of opposed slots 220. For instance, the slots 220 can be opposite each other along the transverse direction T. It should be appreciated of course that the one or more slots 220 can be positioned as desired. The driver 210 can include one or more flanges 213 that project radially out from the driver shaft 212. The one or more flanges 213 are sized to be received in a respective one of the one or more slots 220 when the driver shaft 212 is in a first rotational position. Accordingly, when the driver shaft 212 is in the first rotational position, the at least one flange 213 is aligned with a corresponding one of the at least one slot 220 along the longitudinal direction. The driver shaft 212 can therefore be driven into the lumen 217 of the inner shaft portion 216 in the actuation direction. The at least one flange 213 can travel in the corresponding aligned at least one slot 220 as the driver shaft 212 is driven into the lumen 217 in the actuation direction.

The driver shaft 212 can be driven into the lumen in the actuation direction until the at least one flange 213 enters the void 219 of the outer shaft portion 218. That is, the at least one flange 213 can be driven through the inner shaft portion 216 in the actuation direction. Further movement of the driver shaft 212 in the actuation direction can cause the driver shaft 212 to bear against the second shaft portion 221, which can receive the drive force applied by the driver shaft 212. Thus, the drive force can cause the plunger mechanism 189, and thus the ramps 190, to travel in the actuation direction to the actuated position, thereby deploying the anchors as described above.

When it is desired to return the anchors from the deployed position to the insertion position, the driver shaft 212 can be rotated to a second rotational position that is different than the first rotational position. Rotation of the driver shaft 212 to the second rotational position removes the at least one flange 213 from alignment with the corresponding at least one slot 220. The at least one flange 213 can instead become aligned with a wall of the actuator shaft 196. The aligned wall of the actuator shaft 196 can be defined by the wall of the inner shaft portion 216 when the driver shaft 212 is in the second rotational position. In particular, the wall of the inner shaft portion 216 can be adjacent the at least one flange 213 in the rearward direction, which can define the reverse direction as described above. Thus, subsequent movement of the driver shaft 212 in the reverse direction causes the at least one flange 213 to bear against the wall of the inner shaft portion 216, and thus causes the driver shaft 212 to apply a reverse force to the plunger 189, and thus to the at least one ramp 190. The reverse force is in a direction opposite the actuation force. The driver shaft 212 can therefore drive the plunger 189, and thus the at least one ramp 190, to travel in the reverse direction until the actuator 180 is in the initial position, and the anchors are in the insertion position. Movement of the plunger 189, and thus the at least one ramp 190, in the reverse direction can be achieved by a pulling force applied to the driver shaft 212. The driver shaft 212 can be rotated to the first rotational position, thereby aligning the at least one flange with the corresponding at least one slot 220 along the longitudinal direction, and removed from the actuator shaft 196. Alternatively, it is contemplated that the driver instrument 210 can be captured in the cage body 120, and thus not removable from the cage body in any of the rotational positions. For instance, the driver instrument 210, the cage body 120, the actuator 180, and the anchors 160 and 170 can be manufactured together so as to form a single complete construct.

As illustrated in FIGS. 8B-8C, the outer shaft portion 218 can include one or more stop members 222 that limit rotation of the driver shaft 212 from the first rotational position to the second rotational position. In particular, when the driver shaft 212 enters the void 219 of the outer shaft portion in the first rotational position, the stop member 222 can permit the driver shaft 212 to rotate in a first direction of rotation from the first rotational position to the second rotational position. Interference between the stop member 222 and the at least one flange 213 can prevent the driver shaft 212 from rotating in a second rotational direction opposite the first rotational direction. In one example, the first rotational direction can be defined by the clockwise direction. The stop member 222 can also limit the angular distance that the driver shaft 212 is rotated in the first rotational direction before the driver shaft 212 reaches the second rotational position. In particular, the stop member 222 can abut the at least one flange 213 when the driver shaft 212 has been rotated to the second rotational position, thereby preventing further rotation of the driver shaft 212 in the first rotational direction. In one example, the driver shaft 212 can rotate ninety degrees from the first rotational position to the second rotational position. It should be appreciated, of course, that the driver shaft 212 can rotate any amount as desired from the first rotational position to the second rotational position, such that the at least one flange 213 is not aligned with any of the slots 220 along the longitudinal direction. It should be further appreciated that the driver shaft 212 can also apply the drive force in the actuation direction when the driver shaft 212 is in the second rotational position.

Figure 9A:
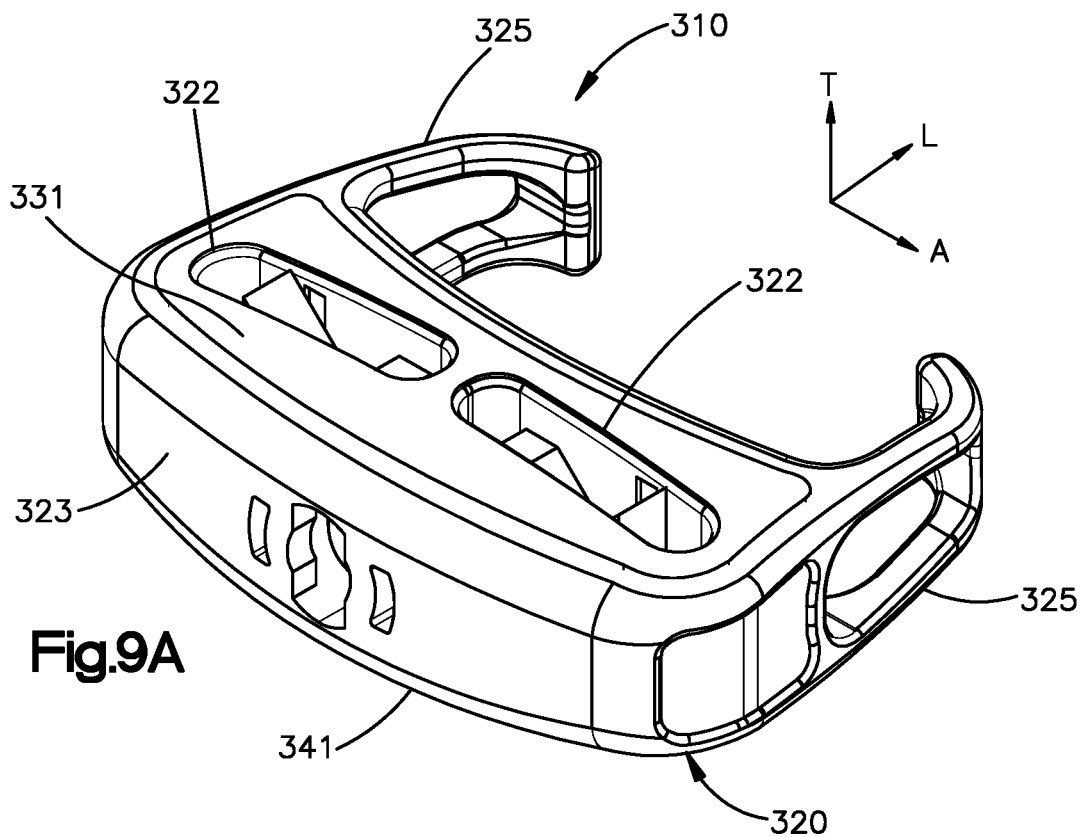
FIG. 9A is a perspective view of an intervertebral cage constructed in accordance with another example, shown in a first or insertion configuration.
Figure 9B:
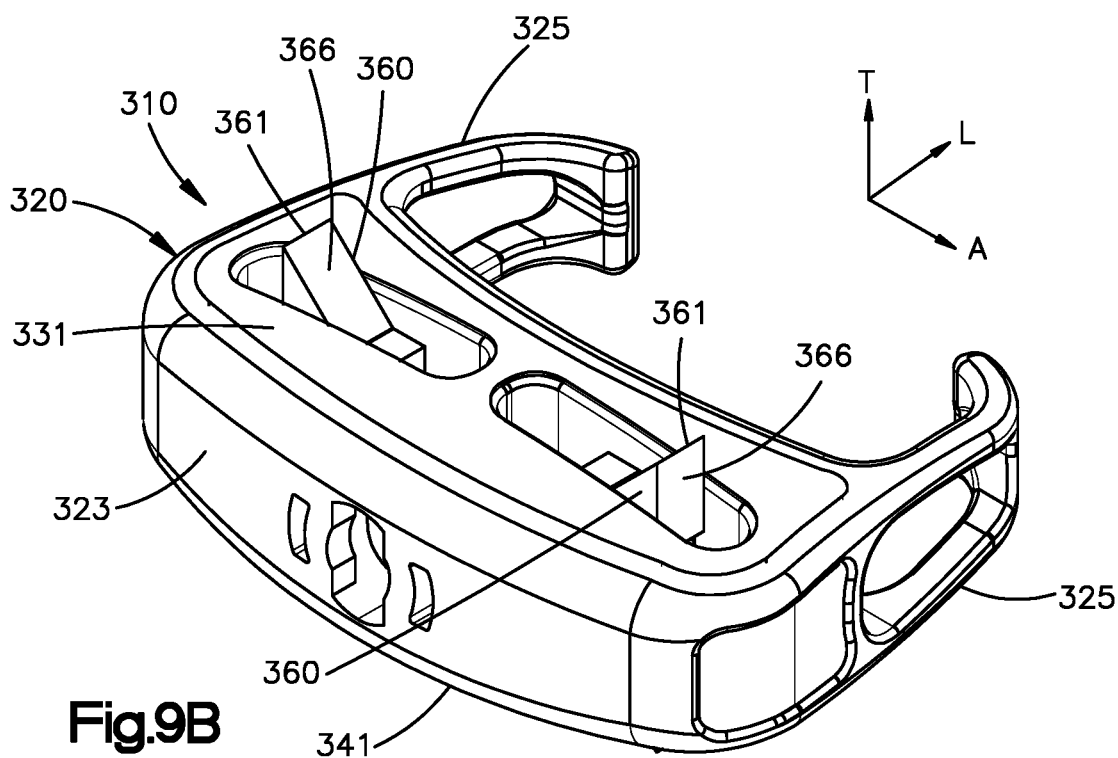
FIG. 9B is a perspective view of the intervertebral cage illustrated in FIG. 9A, showing deployable anchors in a deployed state.
Figure 9E:
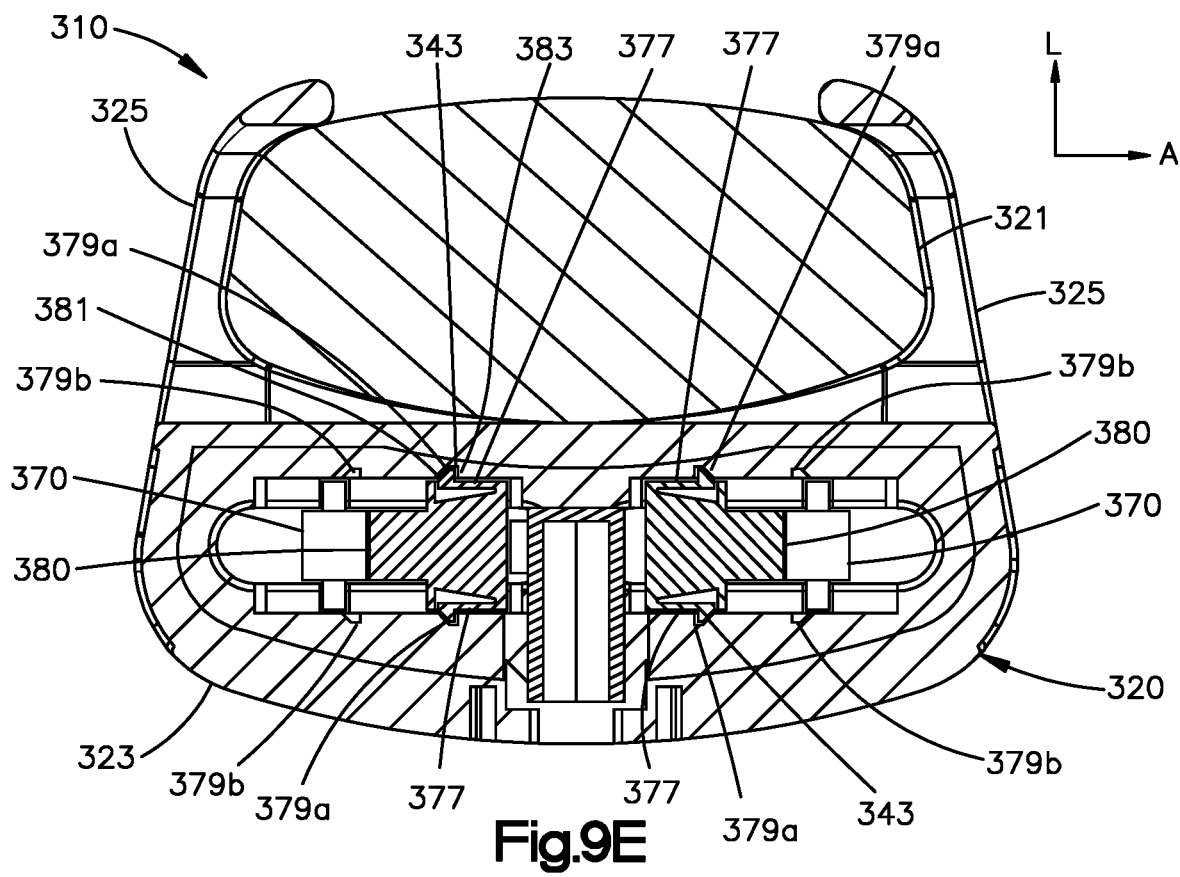
FIG. 9E is a sectional plan view of the intervertebral cage illustrated in FIG. 9A, showing actuators in an initial position.

Referring now to FIGS. 9A-9B, another example of an intervertebral implant or cage 310 can include an implant or cage body 320 that is configured to receive a spacer 321 (see FIG. 9E). In particular, the cage body can include a support member 323 and a pair of arms 325 that extend out from laterally opposed ends of the support member 323. The arms 325 can be spaced from each other along the lateral direction A. The arms 325 can be configured to grip the spacer 321, and the cage 310 can then be inserted into the intervertebral disc space. The spacer 321 can be made from any suitable material, such as polyetheretherketone (PEEK). Alternatively, the spacer 321 can be made from allograft, such as cortical bone, cancellous bone, or a combination of the two. The arms 325 can be constructed in any manner as desired suitable to reliably secure the spacer between the arms 325.

The spacer 321 can facilitate fusion with the superior and inferior vertebrae. Because the spacer 321 can be radiolucent, post-operative CT images can provide good visibility of the fusion between the upper and lower vertebrae and the intervertebral cage 310. In one example, the arms 325 and spacer 321 can be constructed as described in U.S. Pat. No. 9,241,809, the disclosure of which is hereby incorporated by reference as if set forth in its entirety herein. It should be appreciated that the arms 325 can therefore be flexible, or can alternatively be rigid.

The cage body 320 can define an upper bearing surface 331 and a lower bearing surface 341 opposite the upper bearing surface 331 along the transverse direction T. The upper bearing surface is configured to bear against an endplate of a first or superior vertebral body when the intervertebral cage 310 is disposed in the intervertebral disc space. The lower bearing surface 341 is configured to bear against an endplate of a second or inferior vertebral body when the intervertebral cage 310 is disposed in the intervertebral disc space. The support member 323 can include a front surface 323a and a rear surface 323b that is opposite the front surface 323a along the longitudinal direction L. The rear surface 323b is configured to face the spacer 321.

The intervertebral cage 310 can further include one or more deployable first or upper anchors 360 that are configured to penetrate and extend into the superior vertebral body. In one example, the intervertebral cage 310 can include a pair of upper anchors 360. The upper anchors 360 of the pair of upper anchors can be spaced from each other along the lateral direction A. Further, the upper anchors 360 can be aligned with each other along the lateral direction A. The upper anchors 360 can define a first or insertion position shown in FIG. 9A, whereby the anchors 360 are embedded in the cage body 320. For instance, the anchors 360 can be recessed with respect to the upper bearing surface 331 to facilitate insertion of the intervertebral cage 310 into the disc space. Alternatively, the anchors can protrude slightly out from the upper bearing surface 331 so as to roughen the superior vertebral endplate as the cage 310 is inserted into the disc space. The upper anchors 360 can be actuated or deployed to a second or deployed position shown in FIG. 9B, whereby the anchors 360 project through the upper bearing surface 331.

The cage body 320 can define one or more upper retention slots 322 that are configured to retain a respective one or more of the upper anchors 360. For instance, the retention slots 322 can be defined by the support member 322. The upper anchors 360 can ride in the retention slots 322 as they travel between the first or insertion position and the second or deployed position. When the intervertebral cage 310 is disposed in the intervertebral space and the anchors 360 are in the deployed position, the anchors 360 can become embedded in the superior vertebral body. The upper anchors 360 can be configured as teeth 366 that extend out from the upper bearing surface 331 when the anchors 360 are in the second engaged position. The upper teeth 366 can have a sharp, bone-piercing upper edge or tip 361 that is configured to assist in piercing the superior vertebral body so as to embed the anchors 360 in the superior vertebral body. As will be appreciated from the description below, the upper anchors 360 can be configured to be deployed simultaneously in one example.

Referring now to FIGS. 9A and 9D, the intervertebral cage 310 can further include one or more deployable second or lower anchors 370 that are configured to penetrate and extend into the inferior vertebral body. In one example, the intervertebral cage 310 can include a pair of lower anchors 370. The lower anchors 370 of the pair of lower anchors can be spaced from each other along the lateral direction A. Further, the lower anchors 370 can be aligned with each other along the lateral direction A. The lower anchors 370 can define a first or insertion position shown in FIG. 9A, whereby the anchors 370 are embedded in the cage body 320. For instance, the anchors 370 can be recessed with respect to the lower bearing surface 341 to facilitate insertion of the intervertebral cage 310 into the disc space. Alternatively, the lower anchors 370 can protrude slightly out from the lower bearing surface 341 so as to roughen the superior vertebral endplate as the cage 310 is inserted into the disc space. The lower anchors 370 can be actuated or deployed to a second or deployed position (see FIG. 9D), whereby the lower anchors 370 project out from the lower bearing surface 341.

The cage body 320 can define one or more lower retention slots 342 that are configured to retain a respective one or more of the lower anchors 370. For instance, the lower retention slots 342 can be defined by the support member 322. The lower anchors 370 can ride in the retention slots 342 as they travel between the first or insertion position and the second or deployed position. When the intervertebral cage 310 is disposed in the intervertebral space and the anchors 370 are in the deployed position, the anchors 370 can become embedded in the inferior vertebral body. The lower anchors 370 can be configured as teeth 376 that extend out from the lower bearing surface 341 when the anchors 370 are in the second engaged position. The lower teeth 376 can have a sharp, bone-piercing upper edge or tip 371 that is configured to assist in piercing the superior vertebral body so as to embed the anchors 370 in the inferior vertebral body. As will be appreciated from the description below, the lower anchors 370 can be configured to be deployed simultaneously in one example.

It should be appreciated that the geometry of the teeth 366 and 376 can vary as desired. In one example, the sides of the teeth 366 and 376 can be smooth in one example. In another example, the sides of the teeth 366 and 376 can be barbed to assist with fixation in the vertebral body. Further, the respective tips 361 and 371 can be blunt or sharp as desired.

When the upper and lower anchors 360 and 370 are in their first or insertion position, the cage 310 can be said to be in the first or insertion configuration. The cage 310 can be configured to simultaneously deploy the upper anchors 360 and the lower anchors 370.

Referring now to FIGS. 9C-9D, the cage 310 can further include at least one actuator 380 that is supported and captured in the cage body 320, and movable in an actuation direction to deploy the anchors 360 and 370. The actuation direction can be oriented along the lateral direction A in one example. The actuator 380 is movable from a first or initial position in the actuation direction to a second or actuated position. When the actuator 380 is in the initial position, the anchors 360 and 370 can be in their insertion positions. As the actuator 380 is moved from the initial position to the actuated position, the actuator 380 urges the anchors 360 and 370 to their deployed positions. The cage body 320, the actuator 380, and the anchors 360 and 370 can be manufactured together so as to form a single complete construct, as described above.

The actuator 380 can define a first end that can include a force transfer surface 388 that is configured to receive an actuation force from a driver instrument 410 that urges the actuator 380 to travel in the actuation direction. The actuator 380 can further define a second end that is opposite the first end and can include a ramp 390. In one example, the first and second ends of the actuator 380 can be opposite each other along the lateral direction A. The actuator 380 can be driven in an actuation direction that causes the ramp 390 urge the anchors 360 and 370 to their deployed position. In particular, the ramp 390 can define an upper ramped surface 398 and a lower ramped surface 400 opposite the upper ramped surface 398 along the transverse direction. The upper ramped surface 398 can extend down along the transverse direction T as it extends laterally outward toward the upper anchor 360 in a direction away from the first end of the actuator 380, which can define the direction of the drive force. The lower ramped surface 400 can extend up along the transverse direction T as it extends laterally outward toward the lower anchor 360 in a direction away from the first end of the actuator 380, which can define the direction of the drive force. The upper and lower ramped surfaces 398 and 400 can be sloped equally and opposite each other as desired.

When the actuator 380 is in the initial position, the upper and lower ramped surfaces 398 and 400 are aligned with respective bearing surfaces 365 and 375 of the upper and lower anchors 360 and 370 in the actuation direction. For instance, the ramp 390 can define a tapered tip that is aligned with a gap between the bearing surfaces 365 and 375 in the actuation direction. The ramped surfaces 398 and 400 can extend rearwardly from the tapered tip. The upper bearing surface 365 can also define a ramped surface. For instance, the upper bearing surface 365 can be sloped upward as it extends in a direction opposite the actuation direction. Thus, the upper bearing surface 365 can be parallel to the upper ramped surface 398. Similarly, the lower bearing surface 375 can define a ramped surface. For instance, the lower bearing surface 375 can be sloped downward as it extends in the direction opposite the actuation direction. Thus, the lower bearing surface 375 can be parallel to the lower ramped surface 400.

During operation, the actuator 380 is driven in the actuation direction to deploy the upper and lower anchors 360 and 370. In one example, the cage 310 can include first and second actuators 380 that are configured to deploy respective first and second pairs of upper and lower anchors 360 and 370 as they travel in their respective actuation direction. In particular, the first and second actuators 380 can travel away from each other along the lateral direction A as they travel in their respective actuation directions. That is, the actuation direction of the first actuator 380 can be away from the second actuator 380 along the lateral direction A. Similarly, the actuation direction of the second actuator 380 can be away from the first actuator 380 along the lateral direction A. As the actuator 380 is moved in the actuation direction, the upper bearing surface 365 rides along the upper ramped surface 398. The slope of the upper ramped surface 398 urges the corresponding upper tooth 366 outward along the transverse direction T to the deployed position. Similarly, the lower bearing surface 375 rides along the lower ramped surface 400. The slope of the lower ramped surface 400 urges the corresponding lower tooth 376 outward along the transverse direction T to the deployed position.

It should be appreciated that the upper and lower bearing surfaces 365 and 375 can thus be sloped equally and opposite each other. Further, the upper and lower ramped surfaces 398 and 400 can be sloped equally and opposite each other. Alternatively, the upper and lower ramped surfaces 398 and 400 can be sloped opposite each other and at different slopes if it is desired to insert the upper and lower anchors 360 and 370 into the respective superior and inferior vertebrae at different depths.

Figure 9F:
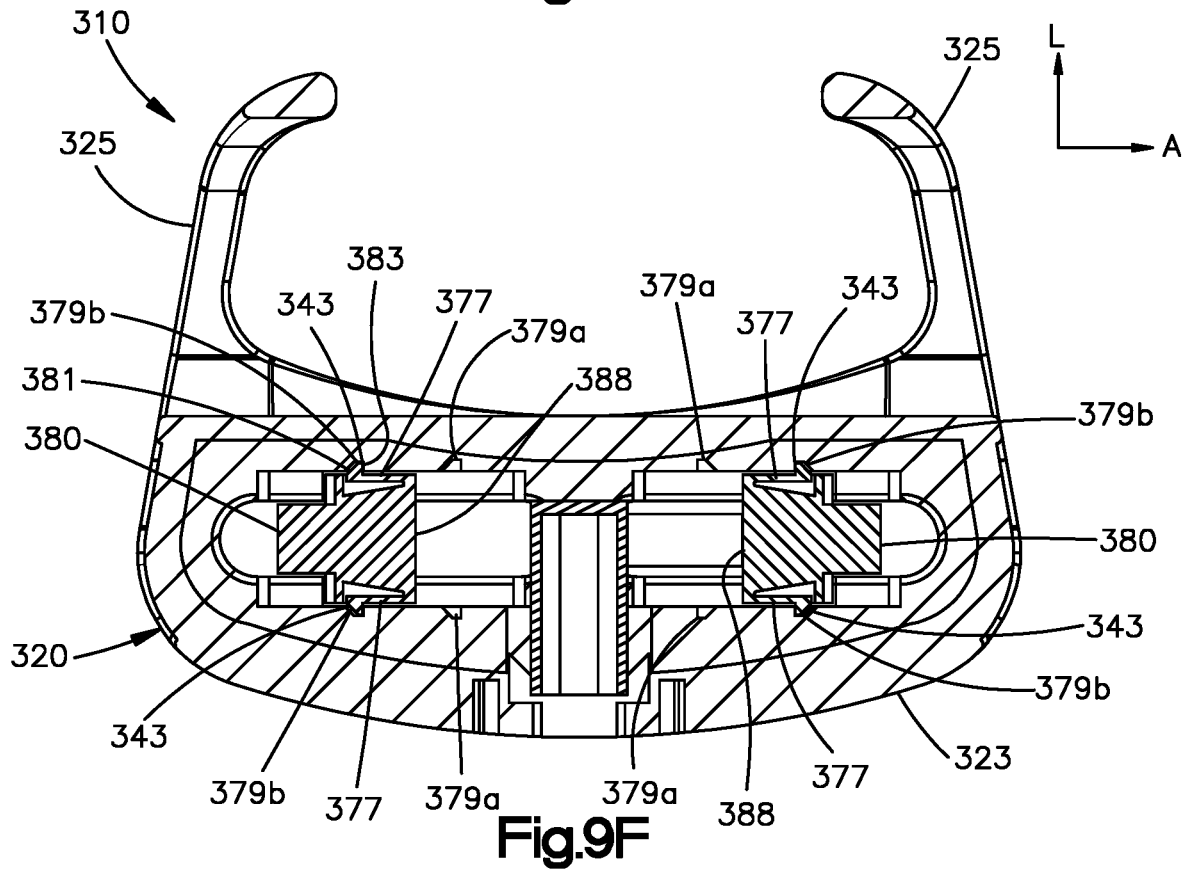
FIG. 9F is a sectional plan view of the intervertebral cage illustrated in FIG. 9B, showing the actuators in an actuated position.

Referring now to FIGS. 9E-9F, the actuators 380 are configured to be retained in their actuated position, which correspondingly retains the upper and lower anchors 360 and 370 in their deployed position. For instance, the actuators 380 can each define at least one retention members that is configured to interlock with the cage body 320 to retain the actuators 380 in the actuated position. For instance, each of the actuators 380 can include a pair of retention members. The retention members can be configured as outwardly projecting retention fingers 377. For instance, the retention fingers 377 can outwardly project in the longitudinal direction. The retention fingers 377 can be resilient and barbed, and configured to be received in retention pockets of the cage body 320. In particular, the cage body 320 can define first retention pockets 379a that are configured to receive the retention fingers 377 when the actuators 380 are in their first or initial position. The barbs 343 of the retention fingers 377 can define a beveled surface 381 that is angled outward away from the respective actuator 380 as it extends in a direction opposite the actuation direction. Thus, as an actuation force is applied to the actuators 380, the barbs 343 can move out of the first retention pockets 379a. The retention fingers 377 can resiliently flex inwardly as the barbs 343 travel out of the first retention pockets 379a. The barbs 343 are received in respective second retention pockets 379b when the actuators 380 are in the respective actuated position. The barbs 343 have a second stop surface 383 opposite the beveled surface 381 that provides a stop surface in the retention pockets 379a and 379b that can prevent movement of the actuators in a reverse direction opposite the actuation direction.

Referring again to FIGS. 9C-9D, and as described above, the cage 310 can further include a driver instrument 410 that is configured to urges one or both of the actuators 380 to travel in the actuation direction. In particular, the driver instrument 410 can include a driver shaft 412, and at least one drive member 414 that extends out from the driver shaft 412. The drive member 414 can be configured to apply a drive force to the force transfer surface 388 of the respective one or both of the actuators 380. In one example, the at least one drive member 414 can be configured as at least one cam member 415 that projects out from the driver shaft 412. In this regard, the driver shaft can be referred to as a cam shaft in some examples. Thus, rotation of the driver shaft 412 can cause the cam member 415 to bear against the force transfer surface 388 of the actuator 380 to drive the actuator 380 from the initial position to the actuated position. The driver instrument 410 can include first and second drive members 414, which can be configured as first and second cam members 415 that are each configured to drive the respective first and second actuators from their respective initial position to their respective actuated position. The driver instrument 410 can be captured in the cage body 320, and can be manufactured together with the cage body 320, the actuators 380, and the anchors 360 and 370 so as to form a single complete construct of the type described above. The cage body 320 can include an opening in 323a that is configured to receive a tool that couples to the driver instrument, and can rotate the driver instrument to drive the actuators 380 to the actuated position.

During operation, each upper tooth 366 rides along the upper ramped surface 198 until it is fully deployed, at which point the fingers 377 are received in the corresponding retention pockets 379b. Similarly, during operation each lower tooth 376 rides along the lower ramped surface 400 until it is fully deployed, at which points the fingers 377 fingers 377 are received in the corresponding retention pockets 379b.

With respect to the ability of the expandable cages to promote fusion, many in-vitro and in-vivo studies on bone healing and fusion have shown that porosity is can facilitate vascularization, and that the desired infrastructure for promoting new bone growth should have a porous interconnected pore network with surface properties that are optimized for cell attachment, migration, proliferation and differentiation. At the same time, there are those who believe the implant's ability to provide adequate structural support or mechanical integrity for new cellular activity is a primary factor to achieving clinical success, while others emphasize the role of porosity as the primary factor. Regardless of the relative importance of one aspect in comparison to the other, what is clear is that both structural integrity to stabilize, as well as the porous structure to support cellular growth, are key components of proper and sustainable bone regrowth.

Accordingly, these cages may take advantage of current additive manufacturing techniques that allow for greater customization of the devices by creating a unitary body that may have both solid and porous features in one. In some embodiments as shown, the cages can have a porous structure, and be made with an engineered cellular structure that includes a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting to change the surface of the device on the nano level. One type of etching process may utilize, for example, HF acid treatment. These same manufacturing techniques may be employed to provide these cages with an internal imaging marker. For example, these cages can also include internal imaging markers that allow the user to properly align the cage and generally facilitate insertion through visualization during navigation. The imaging marker shows up as a solid body amongst the mesh under x-ray, fluoroscopy or CT scan, for example. A cage may comprise a single marker, or a plurality of markers. These internal imaging markers greatly facilitate the ease and precision of implanting the cages, since it is possible to manufacture the cages with one or more internally embedded markers for improved visualization during navigation and implantation.

Another benefit provided by the implantable devices of the present disclosure is that they are able to be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

A variety of spinal implants may be provided by the present disclosure, including interbody fusion cages for use in either the cervical or lumbar region of the spine. Although only an anterior lumbar interbody fusion (ALIF) device is shown, it is contemplated that the same principles may be utilized in a cervical interbody fusion (CIF) device, a transforaminal lumbar interbody fusion (TLIF) device, posterior lumbar interbody fusion (PLIF) cages, lateral lumbar interbody fusion (LLIF) cages, and oblique lumbar interbody fusion (OLIF) cages.

Other embodiments of the disclosure will be apparent to those skilled in the art from consideration of the specification and practice of the disclosure provided herein. It is intended that the specification and examples be considered as exemplary only.

What is claimed is:

1. An intervertebral cage configured to be inserted into an intervertebral disc space defined between first and second vertebral bodies, the intervertebral cage comprising:
   a cage body including an upper plate configured for placement against an endplate of the first vertebral body, and a lower plate configured for placement against an endplate of the second vertebral body;
   an upper cantilever arm having a proximal end and a distal end, and an upper body that is supported at the distal end of the upper cantilever arm, wherein the upper body defines a sloped upper bearing surface;
   an actuator disposed in the cage body, the actuator having an upper ramped surface, wherein the actuator is configured to be driven in an actuation direction from an initial position to an actuated position, which causes the upper bearing surface to ride along the upper ramped surface, thereby driving the upper body away from the lower plate;
   wherein the actuator is captured by the cage body without any external fixation screws when the actuator is in the initial position and as the actuator moves from the initial position to the actuated position, and
   wherein the actuator is configured to receive a drive force directly from a driver instrument that is separate from the cage body, and the drive force causes the actuator to be driven in the actuation direction from the initial position to the actuated position.

2. The intervertebral cage of claim 1, wherein the body has a tapered leading end, and the actuation direction is toward the leading end.

3. The intervertebral cage of claim 1, wherein any one up to all of the upper plate, the lower plate, and a sidewall connecting the upper and lower plates comprises a porous surface.

4. The intervertebral cage of claim 1, wherein the cage body defines an opening configured to receive a driver instrument that is configured to drive the actuator in the actuation direction.

5. The intervertebral cage of claim 1, wherein the upper body moves away from the lower plate against a spring force of the upper cantilever arm.

6. The intervertebral cage of claim 1, comprising a pair of upper bodies, such that movement of the actuator in the actuation direction causes each of the upper bodies to move away from the lower plate.

7. The intervertebral cage of claim 1, further comprising a lower cantilever arm having a proximal end and a distal end, and a lower body that is supported at the distal end of the lower cantilever arm, wherein the lower body defines a sloped lower bearing surface, and movement of the actuator in the actuation direction causes the lower bearing surface to ride along a lower ramp of the actuator, thereby causing the lower body to move away from the upper body.

8. The intervertebral cage of claim 1, wherein the actuator comprises a stop member configured to engage the cage body and a plunger mechanism configured to engage the cage body so as to capture the actuator by the cage body, and the actuator further comprises an actuator spring connected between the stop member and the plunger mechanism.

9. The intervertebral cage of claim 8, wherein the plunger mechanism comprises a ramp that defines the upper ramped surface, wherein the upper body is configured to ride along the upper ramped surface, respectively, as the actuator is driven in the actuation direction.

10. The intervertebral implant assembly comprising:
    the intervertebral cage of claim 1; and
    the driver instrument, wherein the driver instrument is configured to be inserted into the cage in a first rotational position, and rotated to a second rotational position whereby a pulling force applied to the driver instrument in the second rotational position causes the actuator to translate proximally.

11. The intervertebral implant assembly of claim 10, wherein the driver instrument is configured drive the actuator to move the actuator distally both when the driver instrument is in the first rotational position and when the driver instrument is in the second rotational position.

12. The intervertebral cage of claim 1, wherein the upper cantilever arm is secured to the cage body.

13. The intervertebral cage of claim 1, wherein the actuator comprises a retention pocket, and the pocket receives a portion of the upper body when the actuator is in the actuated position.

14. An intervertebral cage configured to be inserted into an intervertebral disc space defined between first and second vertebral bodies, the intervertebral cage comprising:
    a cage body including an upper plate configured for placement against an endplate of the first vertebral body, and a lower plate configured for placement against an endplate of the second vertebral body;
    an upper cantilever arm having a proximal end and a distal end, and an upper body that is supported at the distal end of the upper cantilever arm, wherein the upper body defines a sloped upper bearing surface; and
    an actuator disposed in the cage body, the actuator having an upper ramped surface, wherein the actuator is configured to be driven in an actuation direction from an initial position to an actuated position, which causes the upper bearing surface to ride along the upper ramped surface, thereby driving the upper body away from the lower plate,
    wherein the actuator is disposed in the cage body as the actuator moves from the initial position to the actuated position, and
    wherein the actuator comprises a stop member configured to engage the cage body and a plunger mechanism configured to engage the cage body so as to capture the actuator by the cage body, and the actuator further comprises an actuator spring connected between the stop member and the plunger mechanism.

15. The intervertebral cage of claim 14, wherein the body has a tapered leading end, and the actuation direction is toward the leading end.

16. The intervertebral cage of claim 14, wherein any one up to all of the upper plate, the lower plate, and the sidewall comprises a porous surface.

17. The intervertebral cage of claim 14, wherein the cage body defines an opening configured to receive a driver instrument that is configured to drive the actuator in the actuation direction.

18. The intervertebral cage of claim 14, wherein the upper body moves away from the lower plate against a spring force of the upper cantilever arm.

19. The intervertebral cage of claim 14, further comprising:
- a pair of upper bodies, such that movement of the actuator in the actuation direction causes each of the upper bodies to move away from the lower plate; and
- a lower cantilever arm having a proximal end and a distal end, and a lower body that is supported at the distal end of the lower cantilever arm, wherein the lower body defines a sloped lower bearing surface, and movement of the actuator in the actuation direction causes the lower bearing surface to ride along a lower ramp of the actuator, thereby causing the lower body to move away from the upper body.

20. The intervertebral cage of claim 14, wherein the actuator comprises a retention pocket, and the pocket receives a portion of the upper body when the actuator is in the actuated position.

* * * * *